(12) United States Patent
Lövenich et al.

(10) Patent No.: US 10,658,598 B2
(45) Date of Patent: May 19, 2020

(54) FLUORINATED AROMATIC SMALL MOLECULES AS FUNCTIONAL ADDITIVES FOR DISPERSION OF CONDUCTIVE POLYMERS

(71) Applicant: Heraeus Deutschland GmbH & Co. KG, Hanau (DE)

(72) Inventors: Wilfried Lövenich, Bergisch-Gladbach (DE); Nina Kausch-Busies, Bergisch Gladbach (DE); Sergei A. Ponomarenko, Moskau (RU); Andreas Elschner, Mülheim (DE); Yuriy N. Kononevich, Moskau (RU); Alexey S. Tereshchenko, Moskau (RU)

(73) Assignee: HERAEUS DEUTSCHLAND GMBH & CO. KG., Hanau (DE)

( * ) Notice: Subject to any disclaimer, the term of this patent is extended or adjusted under 35 U.S.C. 154(b) by 0 days.

(21) Appl. No.: 15/525,202

(22) PCT Filed: Nov. 17, 2015

(86) PCT No.: PCT/EP2015/076868
§ 371 (c)(1),
(2) Date: May 8, 2017

(87) PCT Pub. No.: WO2016/079144
PCT Pub. Date: May 26, 2016

(65) Prior Publication Data
US 2017/0365798 A1   Dec. 21, 2017

(30) Foreign Application Priority Data

Nov. 18, 2014   (EP) .................................. 14193716

(51) Int. Cl.
| | |
|---|---|
| *H01L 51/50* | (2006.01) |
| *H01L 51/00* | (2006.01) |
| *C07C 43/29* | (2006.01) |
| *C07C 309/43* | (2006.01) |
| *C07D 321/10* | (2006.01) |
| *H01L 51/42* | (2006.01) |

(52) U.S. Cl.
CPC .......... *H01L 51/0073* (2013.01); *C07C 43/29* (2013.01); *C07C 309/43* (2013.01); *C07D 321/10* (2013.01); *H01L 51/005* (2013.01); *H01L 51/0037* (2013.01); *H01L 51/0052* (2013.01); *H01L 51/42* (2013.01); *H01L 51/5088* (2013.01); *Y02E 10/549* (2013.01)

(58) Field of Classification Search
None
See application file for complete search history.

(56) References Cited

U.S. PATENT DOCUMENTS

2010/0320422 A1* 12/2010 Nakane ................ C07C 309/43
252/500

FOREIGN PATENT DOCUMENTS

| EP | 1405849 | A1 | 4/2004 |
|---|---|---|---|
| EP | 1640372 | A1 | 3/2006 |
| JP | 2006-22210 | * | 8/2006 |
| JP | 2006222010 | A | 8/2006 |
| JP | 2007176921 | A | 7/2007 |

OTHER PUBLICATIONS

Yang Liu, et al., Novel Sulfonated Thin-Film Composite Nonfiltration Membranes with Improved Water Flux for Treatment of Dye Soluitions, Journal of Membrane 194-195 Science, 2012, 218-229.
Cuibo Liu, et al., Selective C4-F Bond Cleavage/C-O Bond Formation of Polyfloruoarenes with Phenols and Benzyl Alcohols, Journael of Fluorine Chemistry 156, 2013, 51-60.
International Search Report issued in PCT/EP2015/076868 dated Apr. 6, 2016.
Jarman et al, "Octafluorotoluene as a Reagent for the Selective Protection of Alcoholic and Phenolic Functions: Synthesis and Cleavage of Perfluorotolyl and Other Perfluoroaryl Ethers of Steroids and Other Model Compounds", J. Chem Research (S), 1985, pp. 114-115.

(Continued)

Primary Examiner — Gregory D Clark
(74) Attorney, Agent, or Firm — Blank Rome LLP

(57) ABSTRACT

The present invention relates to a compound having a general formula selected from the group consisting of formula 1a and 1b, wherein K represents an aromatic or heteroaromatic group in which at least one hydrogen atom may be substituted by a functional groups selected from the group consisting of a sulfonic acid group, a sulfuric acid group, an ammonium group and an aliphatic group; X is selected from the group consisting of a C—C-bond, O, S, SO$_2$ and NR', wherein R' represents a hydrogen or an aliphatic or aromatic group; A represents a fluorinated or perfluorinated aromatic group; n represents an integer in the range from 2 to 6; m represents an integer in the range from 1 to 3. The present invention also relates to a composition comprising this compound, to a process for the preparation of a conductive layer using this composition, to a conductive layer comprising the compound according to the present invention, to electronic components comprising this conductive layer and to the use of the compound according to the present invention as an additive in a hole-injection layer of an OLED or in an organic solar cell.

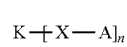

Ia

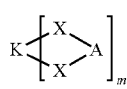

Ib

10 Claims, No Drawings

(56) References Cited

OTHER PUBLICATIONS

Yang et al, "Fluorinated Naphthalocyanines Displaying Simultaneous Reverse Saturable Absorption at 532 and 1064 nm", Advanced Materials, 2005, vol. 17, No. 7, pp. 875-879.

* cited by examiner

FLUORINATED AROMATIC SMALL MOLECULES AS FUNCTIONAL ADDITIVES FOR DISPERSION OF CONDUCTIVE POLYMERS

This application is a national stage of International Patent Application No. PCT/EP2015/076868, filed Nov. 17, 2015, which claims the benefit of European Patent Application 14193716.9, filed Nov. 18, 2014.

The present invention relates to a compound, to a composition comprising this compound, to a process for the preparation of a conductive layer using this composition, to a conductive layer comprising the compound according to the present invention, to electronic components comprising this conductive layer and to the use of the compound according to the present invention as an additive in a hole injection layer of an OLED.

Electrically conducting polymers have been used in a variety of organic electronic devices, including in the development of electroluminescent (EL) devices for use in light emissive displays. With respect to EL devices, such as organic light emitting diodes (OLEDs) containing conducting polymers, such devices generally have the following configuration:

anode/hole injection layer/EL polymer/cathode

The anode is typically any material that has the ability to inject holes into the otherwise filled π-band of the semiconducting, EL polymer, such as, for example, indium/tin oxide (ITO). The anode is optionally supported on a glass or plastic substrate. The EL polymer is typically a conjugated semiconducting polymer such as poly(paraphenylenevinylene) or polyfluorene. The cathode is typically any material (such as, e.g., Ca or Ba) that has the ability to inject electrons into the otherwise empty π*-band of the semiconducting, EL polymer.

The hole injection layer (also referred to as "buffer layer") is typically a conducting polymer and facilitates the injection of holes from the anode into the EL polymer layer. Typical conducting polymers employed as hole injection layer include polyaniline and polydioxythiophenes. A well known conductive polymer that is used to prepare conductive layers in organic electronic devices is a complex of poly(3,4-ethylenedioxythiophene) and polystyrene sulfonic acid, also referred to as "PEDOT/PSS". However, an OLED the hole injection layer which is based on PEDOT/PSS is usually characterized by an unsatisfying performance, in particular by a comparatively short life time and a low efficiency and luminescence.

In order to improve the performance of an OLED the hole injection layer which is based on PEDOT/PSS the prior art suggest to add certain additives to the PEDOT/PSS-dispersions used to form the hole injection layer.

US 2005/0209388 A1, for example, suggest to substitute the polystyrene sulfonic acid by colloid-forming polymeric acids such as NAFION®, wherein according to the teaching of US 2005/0209388 A1 the compositions disclosed therein are obtained by oxidatively polymerizing the thiophene monomers in the presence of NAFION®. US 2004/124504 A1 suggests to improve the performance of an OLED the hole injection layer of which is based on PEDOT/PSS by adding a plurality of nanoparticles to the dispersions. Suitable nanoparticles disclosed in US 2004/124504 A1 are perfluorethylene sulfonates such as NAFION®. However, using NAFION® as an additive in hole injection layers of an OLED has the disadvantage that these fluorinated sulfonic acid polymers are expensive, not soluble in water (they merely form a colloid) and that they are insoluble in organic solvents. These disadvantages limit their compatibility with conductive polymer dispersions especially at higher concentration.

WO 2009/096352 A1 discloses a "charge transport varnish" comprising specific low molecular weight fluorinated sulfonic acids and conductive polymers such as polyanilline. This varnish may have a beneficial effect on OLED performance (i.e. low-voltage drive and luminescence efficiency) if applied as a thin film. The fluorinated sulfonic acids are soluble in water and in highly polar organic solvents such as DMF. A general applicability of these substances has not be shown, in particularly a beneficial effect of the described low molecular weight fluorinated sulfonic acids when used in combination with PEDOT/PSS. Moreover, the solubility of the fluorinated sulfonic acids disclosed in WO 2009/096352 A1 in solvents other than water is low.

It was therefore an object of the present invention to overcome the disadvantages of the prior art in the field of organic electronic devices, in particular of OLEDs the hole injection layer of which is based on conductive polymers such as PEDOT/PSS.

In particular, it was an object of the present invention to provide a low molecular weight additive with a tailored solubility in water or organic solvents that, when used in combination with conductive polymers such as PEDOT/PSS for the preparation of conductive layers in organic electronic devices, in particular for the preparation of a hole injection layer in an OLED, helps to improve the performance of these electronic devices. In contrast to complex polymers such as NAFION® the low-molecular weight additives should by obtainable by a simple 1-2 step synthesis from commercially available precursors.

A contribution to the solution of at least one of the above objects is provided by the subject matter of the category-forming independent claims, wherein the therefrom dependent subclaims represent preferred embodiments of the present invention, whose subject matter likewise make a contribution to solving at least one object.

EMBODIMENTS

I. A compound having a general formula selected from the group consisting of formula Ia and Ib

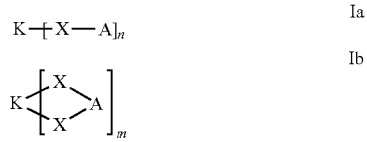

wherein

K represents an aromatic or heteroaromatic group in which in which at least one hydrogen atom may be substituted by a functional groups selected from the group consisting of a sulfonic acid group, a sulfuric acid group, an ammonium group and an aliphatic group;

X is selected from the group consisting of a C—C bond, O, S, SO$_2$ and NR', wherein R' represents a hydrogen or an aliphatic or aromatic group;

A represents a fluorinated or perfluorinated aromatic group;

n represents an integer in the range from 2 to 6;

m represents an integer in the range from 1 to 3.

II. The compound according to embodiment I, wherein the functional group is selected from the group consisting of
  i) —$SO_3M$, wherein M is selected from the group consisting of $H^+$, $Na^+$, $K^+$, $Li^+$, $NH_4^+$, $Ca^{2+}$ and $Mg^{2+}$,
  ii) —$OSO_3M$, wherein M is selected from the group consisting of $H^+$, $Na^+$, $K^+$, $Li^+$, $NH_4^+$, $Ca^{2+}$ and $Mg^{2+}$,
  iii) —$CO_2M$, wherein M is selected from the group consisting of $H^+$, $Na^+$, $K^+$, $Li^+$, $NH_4^+$, $Ca^{2+}$ and $Mg^{2+}$,
  iv) an ammonium group selected from the group consisting of —$N(CH_3)_4^+$, —$N(CH_2CH_3)_4^+$, —$N(C_3H_7)_4^+$, —$N(C_4H_9)_4^+$, and —$N(C_5H_{11})_4^+$, and
  v) an alkyl group selected from the group consisting of —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —$C_{11}H_{23}$ and —$C_{12}H_{25}$.
III. The compound according to embodiment I or II, wherein R' is selected from the group consisting of —$CH_3$, —$C_2H_5$, —$C_3H_7$ and —$C_4H_9$.
IV. The compound according to anyone of embodiments I to III, wherein K represents a monocyclic aromatic or heteroaromatic group and wherein the structural subunit Ia' of formula Ia or the structural subunit Ib' of formula Ib

Ia'

Ib' have a general structure selected from the group consisting of general formulae IIa to IIk (for a monocyclic aromatic group K) or from the group consisting of general formula III to IIx (for a monocyclic heteroaromatic group K):

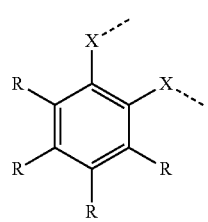

IIa

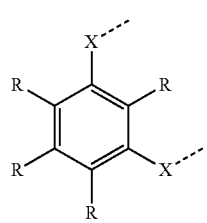

IIb

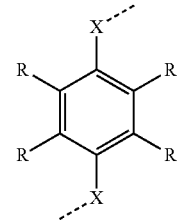

IIc

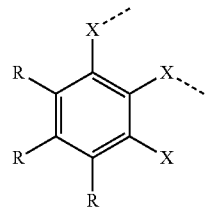

IId

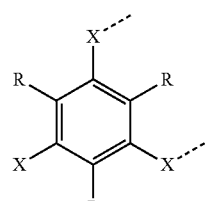

IIe

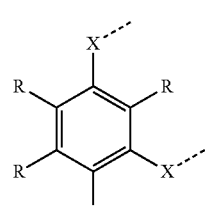

IIf

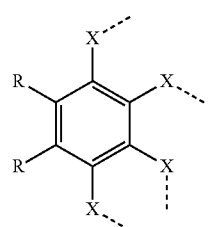

IIg

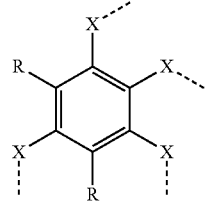

IIh

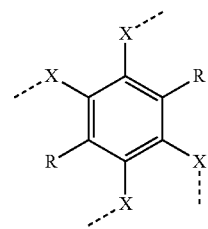

IIj

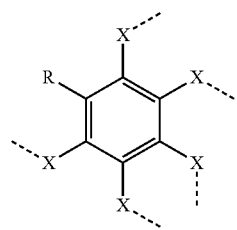
IIk

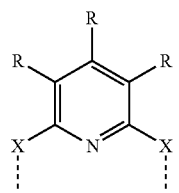
IIl

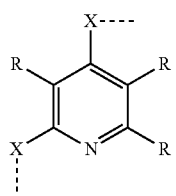
IIm

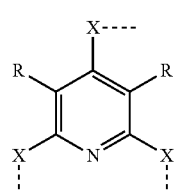
IIn

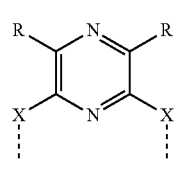
IIo

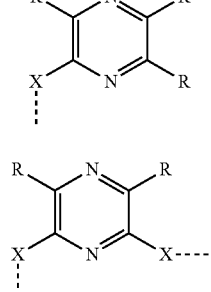
IIp

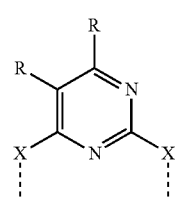
IIq

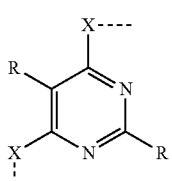
IIr

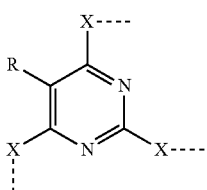
IIs

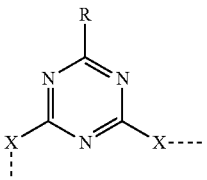
IIt

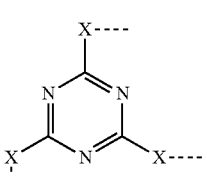
IIu

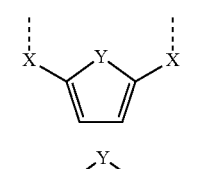
IIv

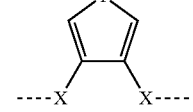
IIw

IIx wherein
Y represents S, O or NR", wherein R" represents a hydrogen atom or an aliphatic group with 1 to 20 carbon atoms,
R is selected from the group consisting of H, —SO$_3$M, —OSO$_3$M, —CO$_2$M, —N(CH$_3$)$_4^+$, —N(CH$_2$CH$_3$)$_4^+$, —N(C$_3$H$_7$)$_4^+$, —N(C$_4$H$_9$)$_4^+$, —N(C$_5$H$_{11}$)$_4^+$, —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —C$_{11}$H$_{23}$, and —C$_{12}$H$_{25}$,
wherein M is as defined in embodiment II and
wherein the dotted line indicates the bond to A.

V. The compound according to embodiment IV, wherein X represents O and wherein the following combinations for substituent R per entity K are fulfilled:
n=2, and
R=1×—SO$_3$M and 3×H or R=2×—SO$_3$M and 2×H, or
n=3, and
R=3×H or R=3×—SO$_3$M,
wherein M is as defined in embodiment II.

VI. The compound according to anyone of embodiments I to III, wherein K represents a bicyclic aromatic or heteroaromatic group, n represents 2 and wherein the structural subunit Ia' of formula Ia or the structural subunit Ib' of formula Ib

Ia'

Ib' have a general structure selected from the group consisting of general formulae IIIa to IIIj (for a bicyclic aromatic group K) or from the group consisting of general formula IIIk to IIIu (for a bicyclic heteroaromatic group K):

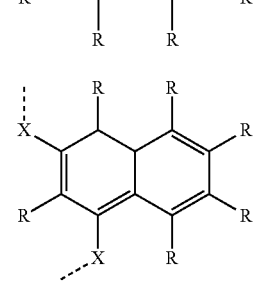

IIIa

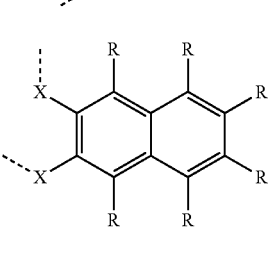

IIIb

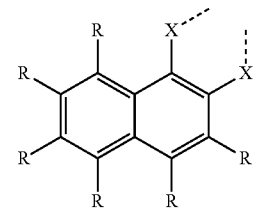

IIIc

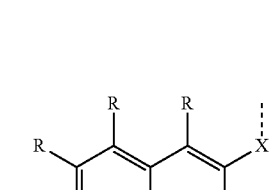

IIId

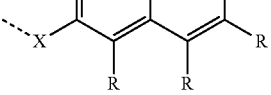

IIIe

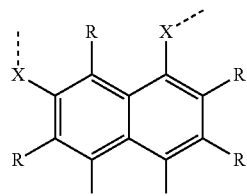

IIIf

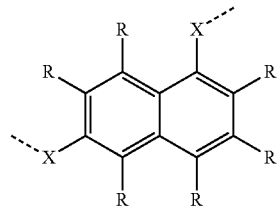

IIIg

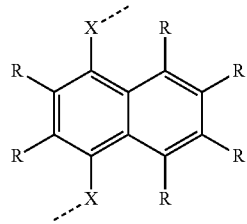

IIIh

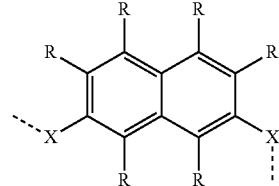

IIIi

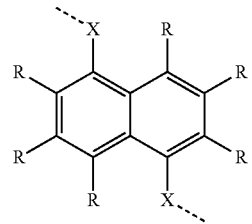

IIIj

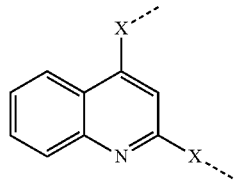

IIIk

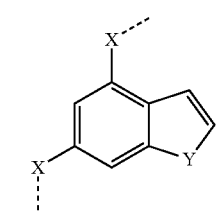

IIIl

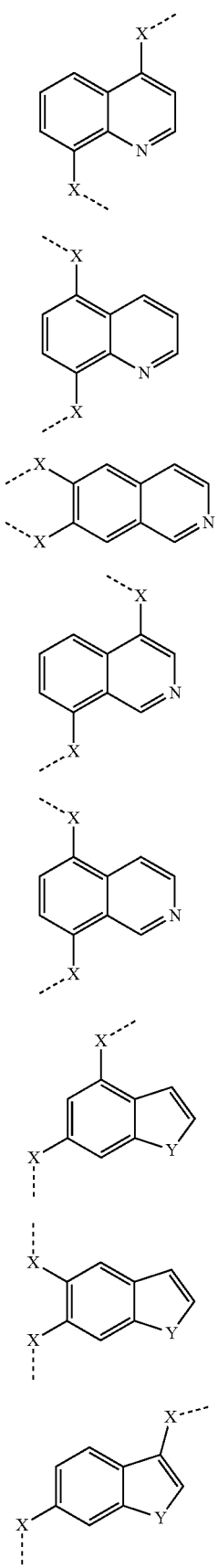

IIIm
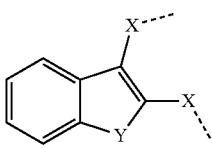

IIIu wherein
Y represents S, O or NR", wherein R" represents a hydrogen atom or an aliphatic group with 1 to 20 carbon atoms, R is selected from the group consisting of H, —SO$_3$M, —OSO$_3$M, —CO$_2$M, —N(CH$_3$)$_4{}^+$, —N(CH$_2$CH$_3$)$_4{}^+$, —N(C$_3$H$_7$)$_4{}^+$, —N(C$_4$H$_9$)$_4{}^+$, —N(C$_5$H$_{11}$)$_4{}^+$, —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —C$_{11}$H$_{23}$, and —C$_{12}$H$_{25}$, wherein M is as defined in embodiment II and wherein the dotted line indicates the bond to A.

VII. The compound according to embodiment VI, wherein X represents O and wherein the following combinations for substituent R per entity K are fulfilled:

R=2×—SO$_3$M and 4×H,
or
R=3×—SO$_3$M and 3×H, wherein M is as defined in embodiment II.

VIII. The compound according to anyone of embodiments I to III, wherein K represents a bicyclic aromatic or heteroaromatic group, n represents 3 and wherein the structural subunit Ia' of formula Ia or the structural subunit Ib' of formula Ib $$K\!-\!\!+\!X]_n \qquad \text{Ia'}$$

$$K\!\!\left\{\!\!\begin{array}{c}X\\X\end{array}\!\!\right]_m \qquad \text{Ib'}$$

have a general structure selected from the group consisting of general formulae IVa to IVl (for a bicyclic aromatic group K) or from the group consisting of general formula IVm and IVn (for a bicyclic heteroaromatic group K):

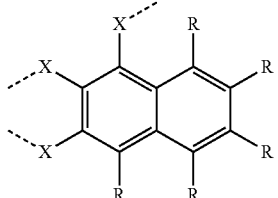

IVa

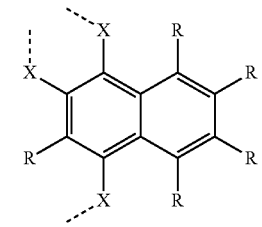

IVb

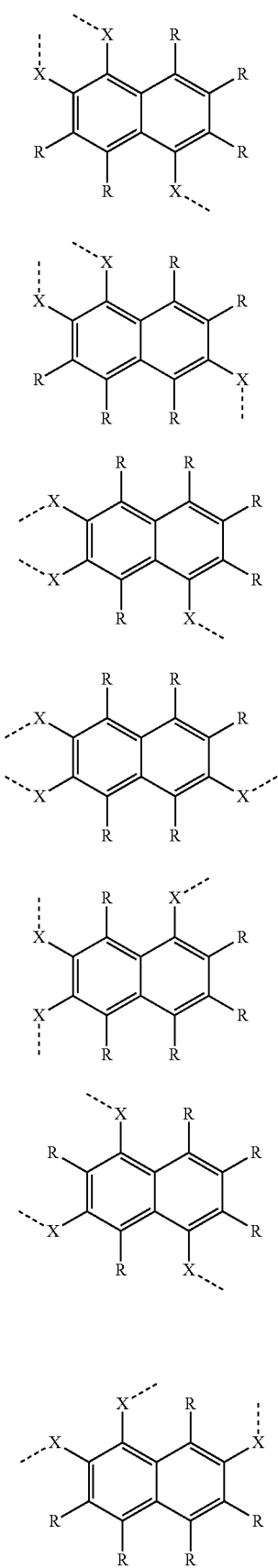
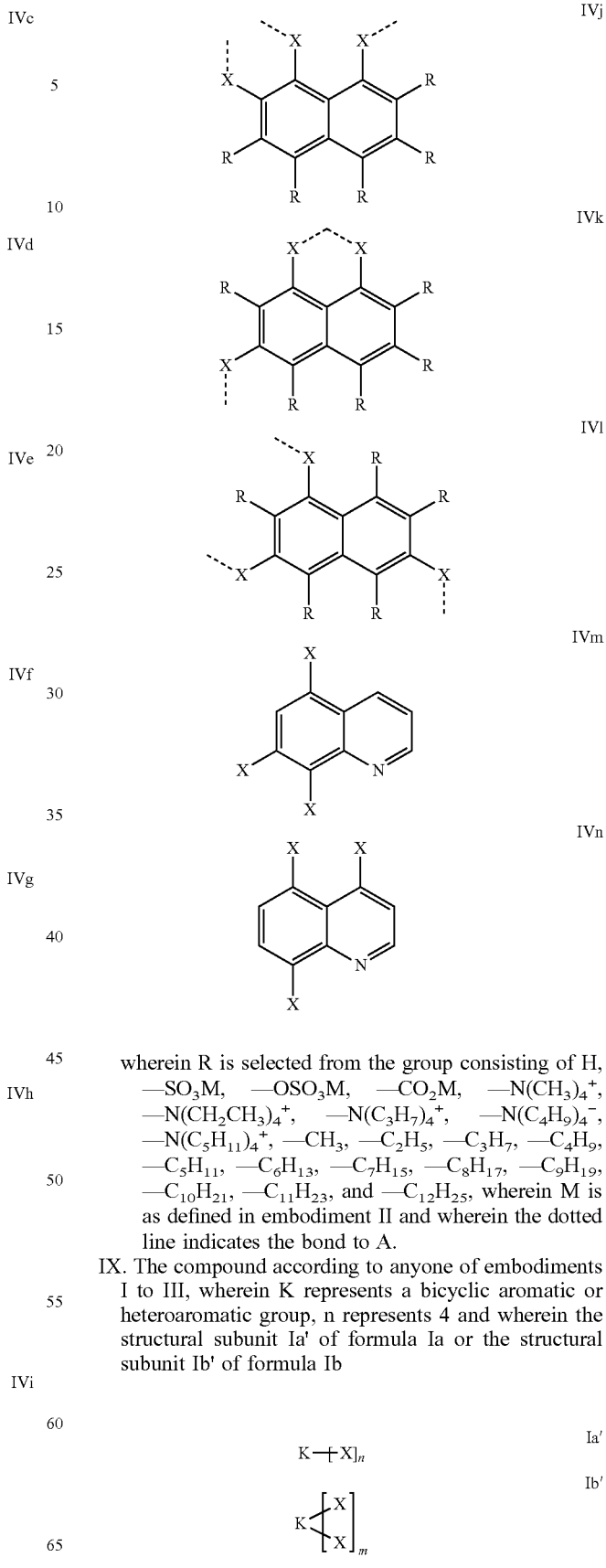

wherein R is selected from the group consisting of H, —SO$_3$M, —OSO$_3$M, —CO$_2$M, —N(CH$_3$)$_4^+$, —N(CH$_2$CH$_3$)$_4^+$, —N(C$_3$H$_7$)$_4^+$, —N(C$_4$H$_9$)$_4^-$, —N(C$_5$H$_{11}$)$_4^+$, —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —C$_{11}$H$_{23}$, and —C$_{12}$H$_{25}$, wherein M is as defined in embodiment II and wherein the dotted line indicates the bond to A.

IX. The compound according to anyone of embodiments I to III, wherein K represents a bicyclic aromatic or heteroaromatic group, n represents 4 and wherein the structural subunit Ia' of formula Ia or the structural subunit Ib' of formula Ib have a general structure selected from the group consisting of general formulae Va to Vi:

Va
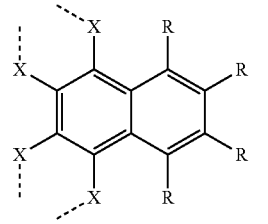

Vb
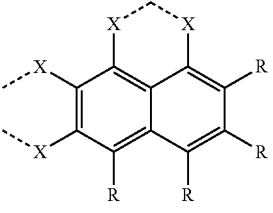

Vc
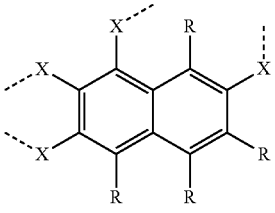

Vd
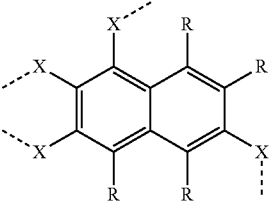

Ve
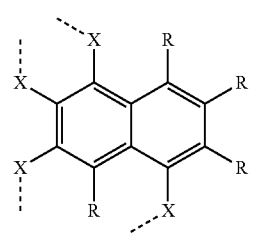

Vf
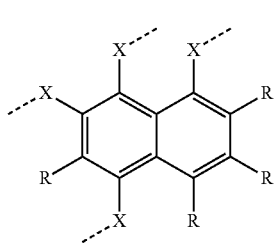

Vg
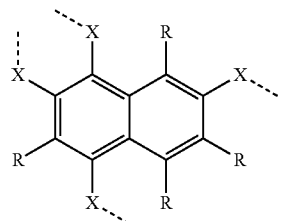

Vh
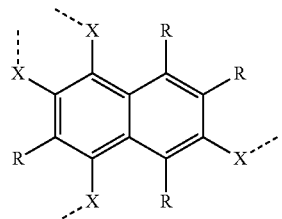

Vi
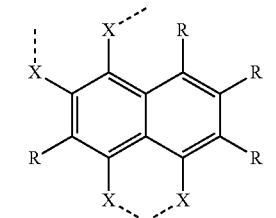

wherein R is selected from the group consisting of H, —SO$_3$M, —OSO$_3$M, —CO$_2$M, —N(CH$_3$)$_4^+$, —N(CH$_2$CH$_3$)$_4^+$, —N(C$_3$H$_7$)$_4^+$, —N(C$_4$H$_9$)$_4^-$, —N(C$_5$H$_{11}$)$_4^+$, —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —C$_{11}$H$_{23}$, and —C$_{12}$H$_{25}$, wherein M is as defined in embodiment II and wherein the dotted line indicates the bond to A.

X. The compound according to anyone of embodiments I to III, wherein K represents a bicyclic aromatic or heteroaromatic group, n represents 5 and wherein the structural subunit Ia' of formula Ia or the structural subunit Ib' of formula Ib Ia'
Ib'

have a general structure selected from the group consisting of general formulae VIa to VIe:

VIa
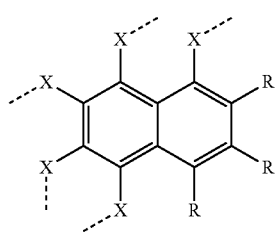

VIb

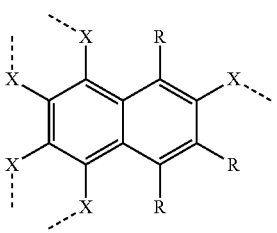

VIc

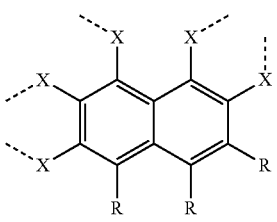

VId

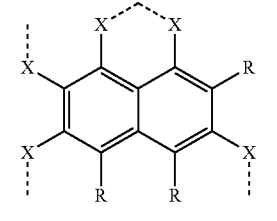

VIe

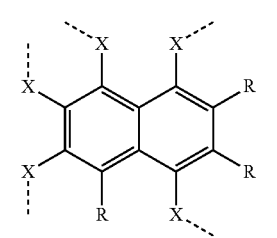

wherein R is selected from the group consisting of H, —$SO_3M$, —$OSO_3M$, —$CO_2M$, —$N(CH_3)_4^+$, —$N(CH_2CH_3)_4^+$, —$N(C_3H_7)_4^+$, —$N(C_4H_9)_4^-$, —$N(C_5H_{11})_4^+$, —$CH_3$, —$C_2H_5$, —$C_3H_7$, —$C_4H_9$, —$C_5H_{11}$, —$C_6H_{13}$, —$C_7H_{13}$, —$C_8H_{17}$, —$C_9H_{19}$, —$C_{10}H_{21}$, —$C_{11}H_{23}$ and —$C_{12}H_{25}$, wherein M is as defined in embodiment II and wherein the dotted line indicates the bond to A.

XI. The compound according to anyone of embodiments I to III, wherein K represents a bicyclic aromatic or heteroaromatic group, n represents 6 and wherein the structural subunit Ia' of formula Ia or the structural subunit Ib' of formula Ib Ia'

$$K{\pmb-}{\lbrack}X{\rbrack}_n$$

Ib'

$$K{\begin{bmatrix}X\\X\end{bmatrix}}_m$$

have a general structure selected from the group consisting of general formulae VIIa to VIIj:

VIIa

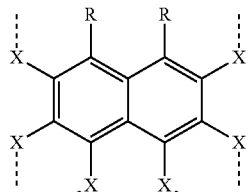

VIIb

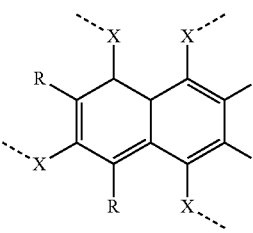

VIIc

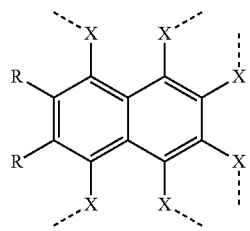

VIId

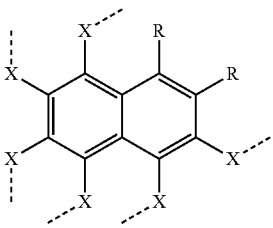

VIIe

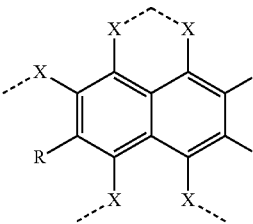

VIIf

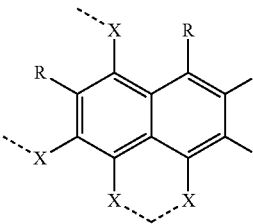

VIIg

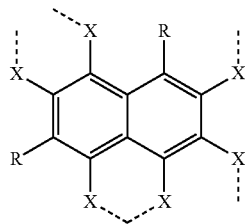

-continued

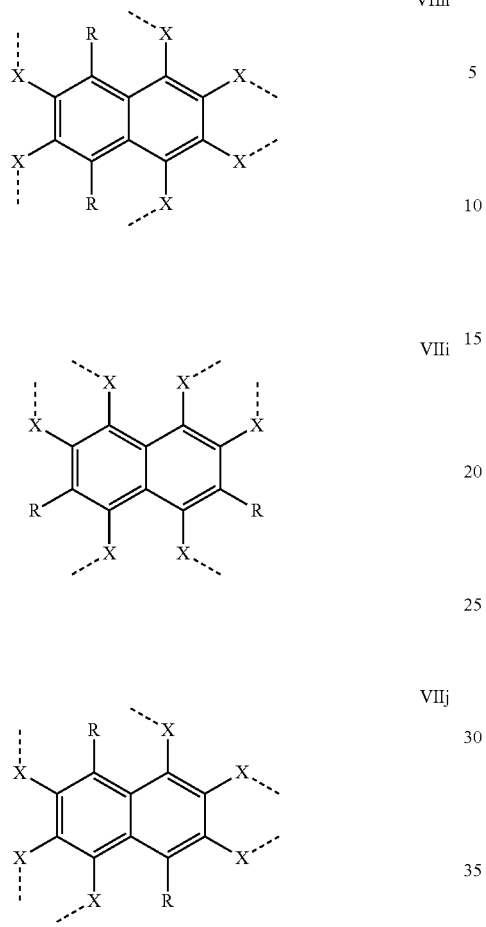

VIIh

VIIi

VIIj wherein R is selected from the group consisting of H, —SO₃M, —OSO₃M, —CO₂M, —N(CH₃)₄⁺, —N(CH₂CH₃)₄⁺, —N(C₃H₇)₄⁺, —N(C₄H₉)₄⁻, —N(C₅H₁₁)₄⁺, —CH₃, —C₂H₅, —C₃H₇, —C₄H₉, —C₅H₁₁, —C₆H₁₃, —C₇H₁₅, —C₈H₁₇, —C₉H₁₉, —C₁₀H₂₁, —C₁₁H₂₃ and —C₁₂H₂₅, wherein M is as defined in embodiment II and wherein the dotted line indicates the bond to A.

XII. The compound according to anyone of embodiments I to III, wherein K represents a tricyclic aromatic or heteroaromatic group and wherein the structural subunit Ia' of formula Ia or the structural subunit Ib' of formula Ib

Ia'

Ib' have a general structure selected from the group consisting of general formulae VIIIa to VIIIr (for a tricyclic aromatic group K) or have the general formula VIIIs to VIIIu (for a tricyclic heteroaromatic group K):

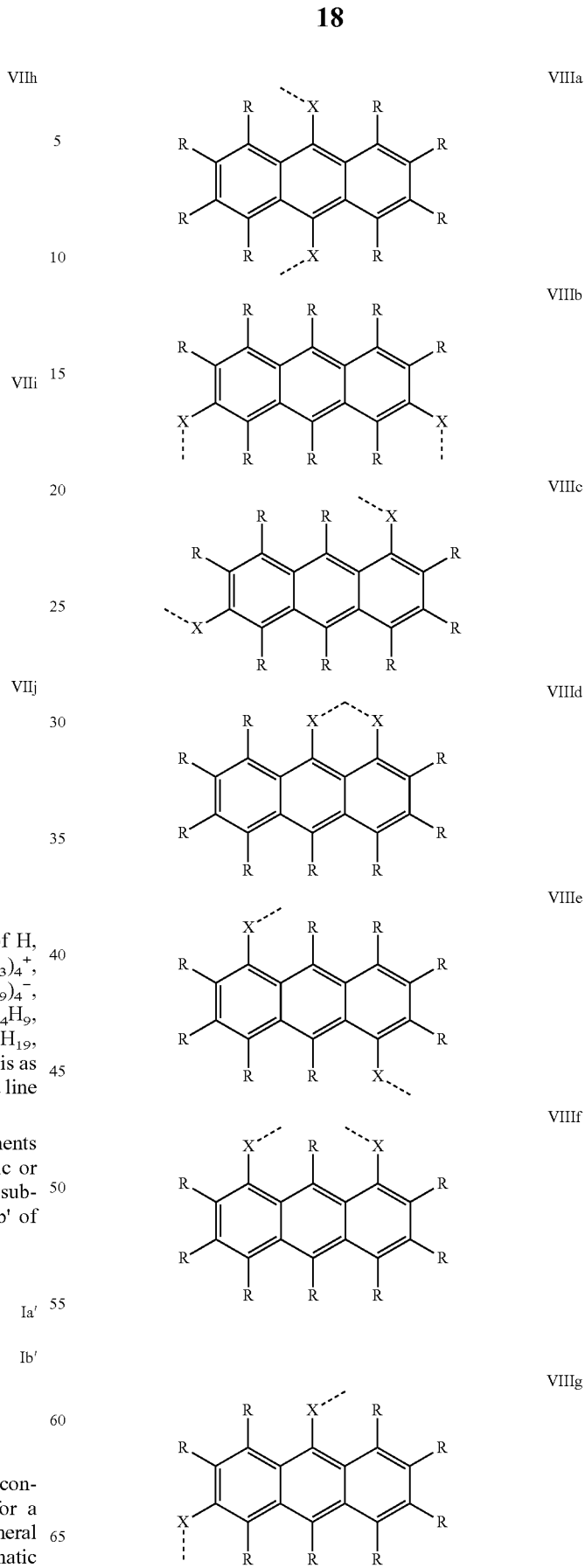

VIIIa

VIIIb

VIIIc

VIIId

VIIIe

VIIIf

VIIIg

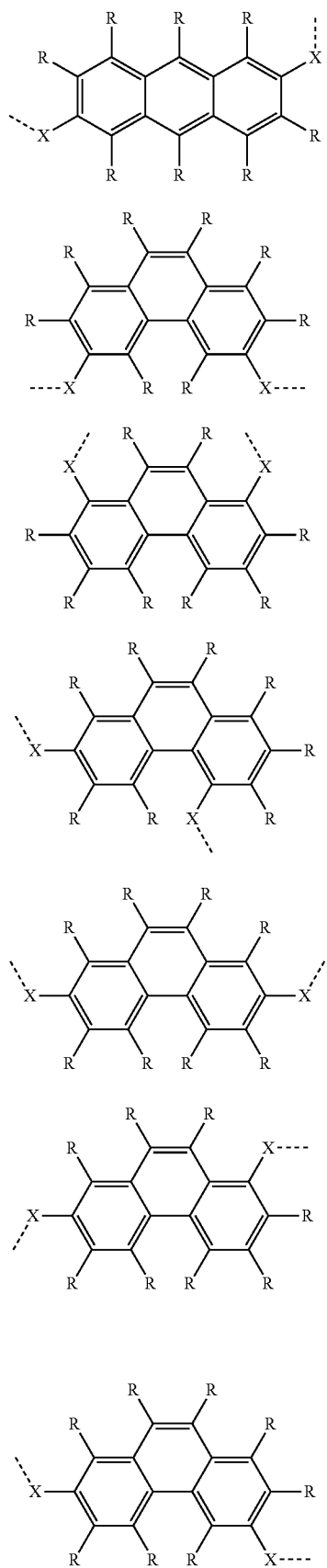
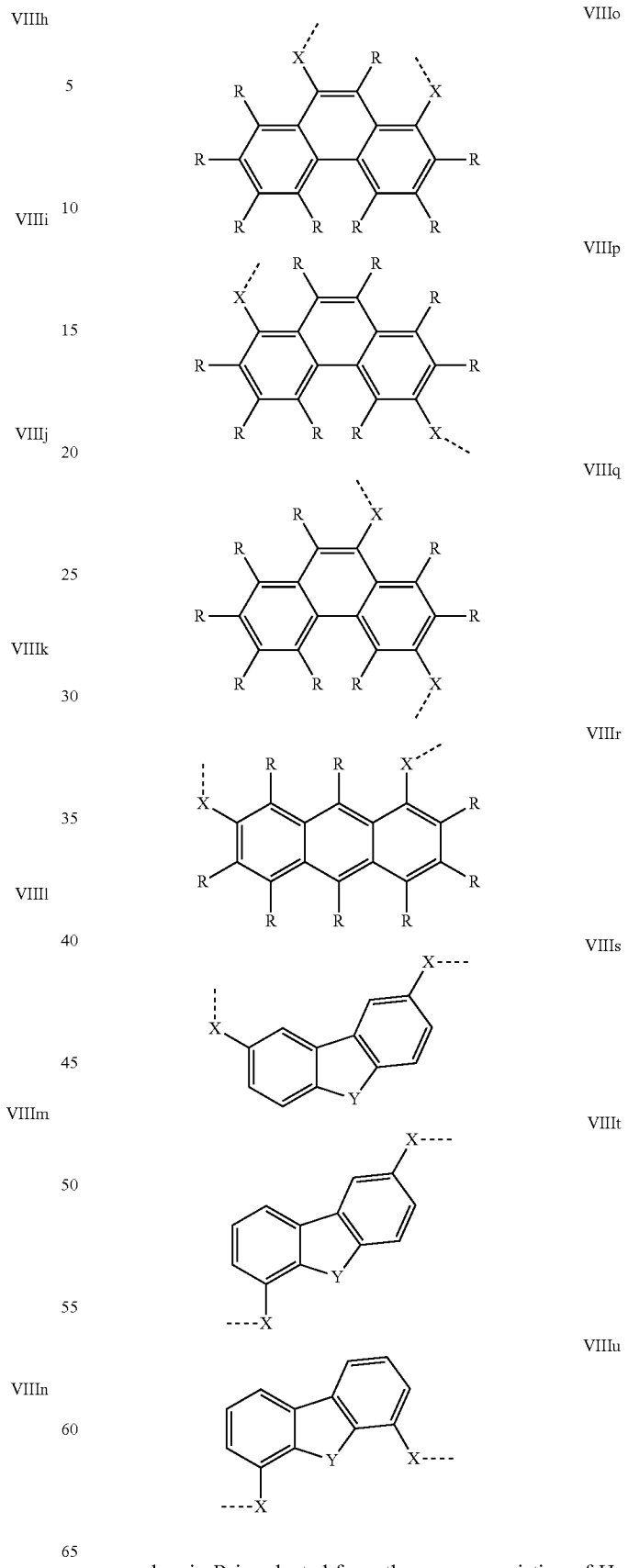
wherein R is selected from the group consisting of H, $-SO_3M$, $-OSO_3M$, $-CO_2M$, $-N(CH_3)_4^+$, —N(CH$_2$CH$_3$)$_4$$^+$, —N(C$_3$H$_7$)$_4$$^+$, —N(C$_4$H$_9$)$_4$$^-$, —N(C$_5$H$_{11}$)$_4$$^+$, —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —C$_{11}$H$_{23}$ and —C$_{12}$H$_{25}$, wherein M is as defined in embodiment II and wherein the dotted line indicates the bond to A.

XIII. The compound according to anyone of embodiments I to XII, wherein A has a general structure selected from the group consisting of general formulae IXa to IXo:

IXa
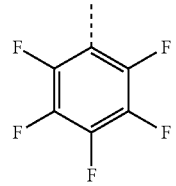

IXb
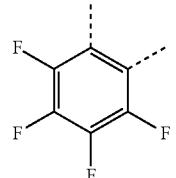

IXc
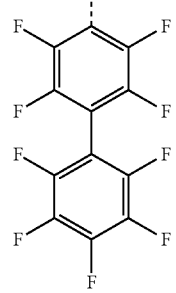

IXd
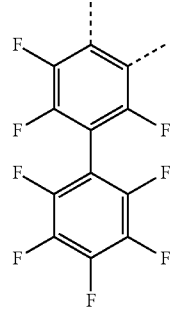

IXe
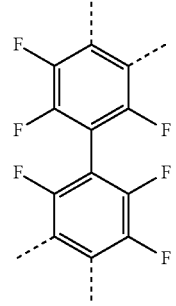

-continued

IXf
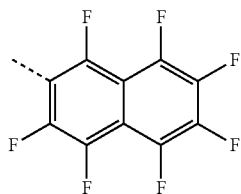

IXg
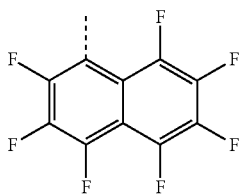

IXh
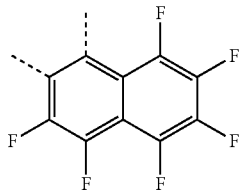

IXi
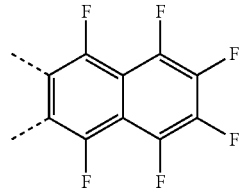

IXj
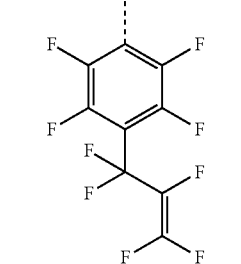

IXk
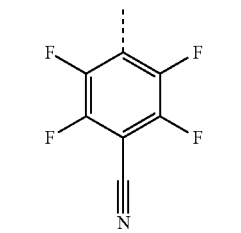

IXl
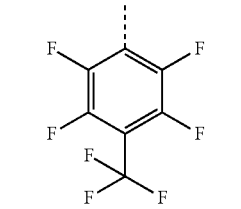

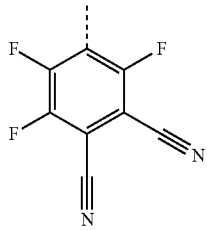
IXm
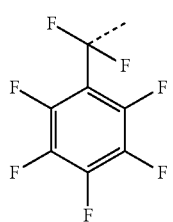
IXn
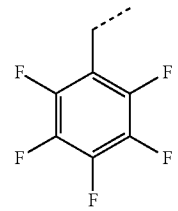
IXo
wherein the dotted line indicates the bond to X.
XIV. The compound according to anyone of embodiments I to XIII, wherein the compound has a general structure selected from the group consisting of general formulae Xa to Xg or the corresponding salts thereof:
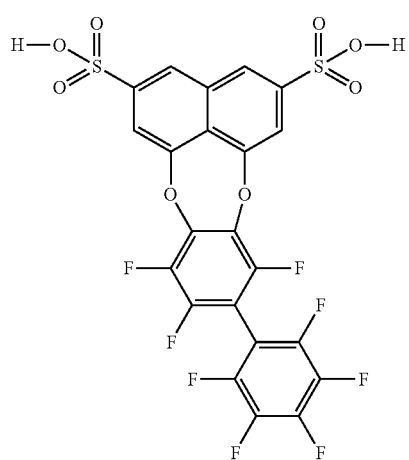
Xa
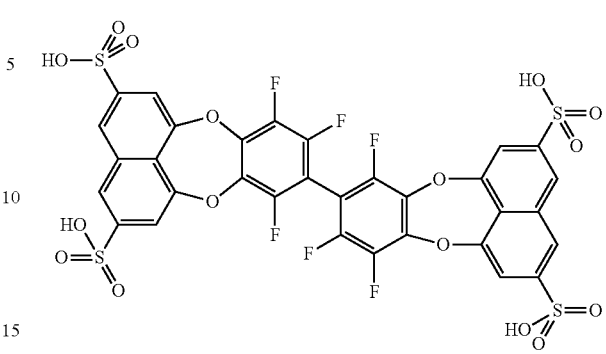
Xb
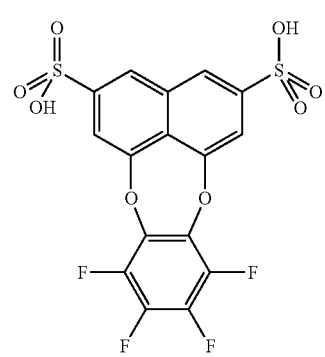
Xc
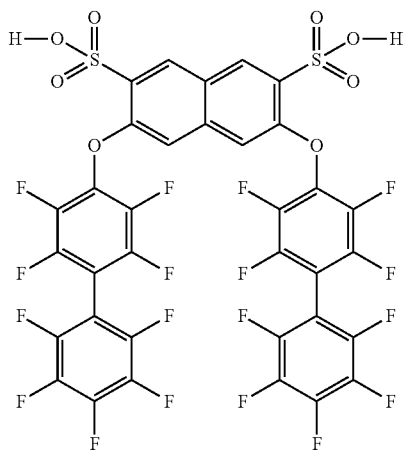
Xd
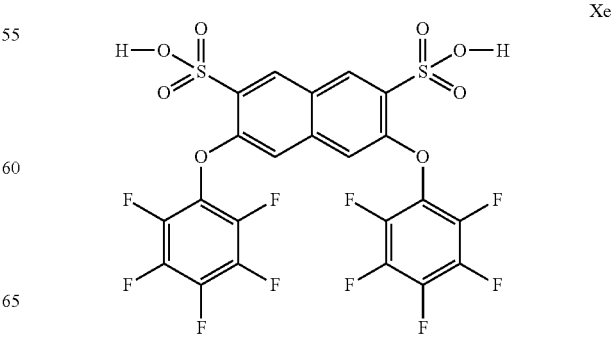
Xe

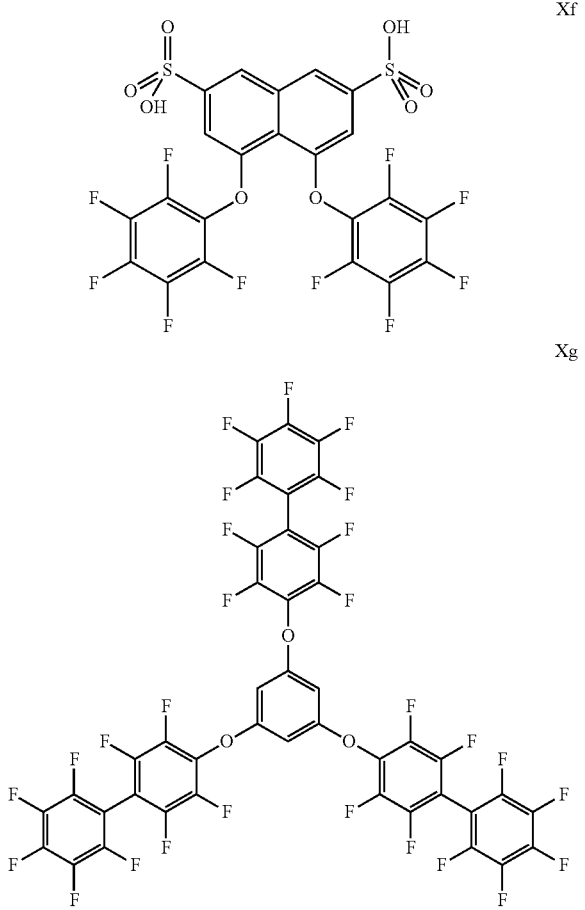

XV. A composition comprising
- I) at least one conductive polymer,
- II) at least one solvent and
- III) at least one compound according to anyone of embodiments I to XIV.

XVI. The composition according to embodiment XV, wherein the conductive polymer I) comprises a polythiophene.

XVII. The composition according to anyone of embodiments XV and XVI, wherein the solvent II) is water, an organic solvent selected from the group consisting of alcohols, aliphatic hydrocarbons, aromatic hydrocarbons, ethers, halogenated hydrocarbons, aliphatic nitriles, aliphatic carboxylic acids, aliphatic carboxylic acid and ketones or a mixture of at least two of these solvents.

XVIII. A process for the preparation of a conductive layer, comprises the process steps:
- (P1) superimposing a substrate with the composition according to anyone of embodiment XV to XVII; or
  - first superimposing a substrate with a composition comprising the solvent and the compound according to anyone of embodiments I to XIV, at least partial removal of the solvent and then superimposing the substrate with a composition according to anyone of embodiments XV to XVII or with a composition comprising the solvent and the conductive polymer; or
  - first superimposing a substrate with a composition comprising the solvent and the conductive polymer, at least partial removal of the solvent and then superimposing the substrate with the composition according to anyone of embodiments XV to XVII or with a composition comprising the solvent the compound according to anyone of embodiments I to XIV;
- (P2) at least partial removal of the solvent.

XIX. A conductive layer comprising at least one compound according to anyone of embodiments I to XIV.

XX. An electronic component comprising a conducting layer obtainable by the process according to embodiment XVIII or comprising a conductive layer according to embodiments XIX.

XXI. The electronic component according to embodiments XX, wherein the electronic component is an OLED, a display, an organic solar cell, a hybrid solar cell, a field effect transistor, or a thermoelectric generator.

XXII. Use of at least one compound according to anyone of embodiments I to XIV as an additive in a hole-injection layer of an OLED or in an organic solar cell.

A contribution towards solving these objects is made by a compound having a general formula selected from the group consisting of formula Ia and Ib

   Ia

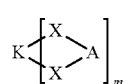   Ib wherein
K represents an aromatic or heteroaromatic group, preferably a mono-, di- or tricyclic aromatic or heteroaromatic group, in which at least one hydrogen atom may be substituted by a functional group selected from the group consisting of a sulfonic acid group, a sulfuric acid group, an ammonium group and an aliphatic group;

X is selected from the group consisting of a C—C bond, O, S, $SO_2$ and NR', preferably selected from the group consisting of O, S, $SO_2$ and NR', wherein R' represents a hydrogen or an aliphatic or aromatic group, preferably an alkyl group and most preferably an alkyl group selected from the group consisting of —$CH_3$, —$C_2H_5$, —$C_3H_7$ and —$C_4H_9$, wherein it is most preferred that X represents O;

A represents a fluorinated or perfluorinated aromatic group;

n represents an integer in the range from 2 to 6, preferably 2 or 3;

m represents an integer in the range from 1 to 3, preferably 1.

It is preferred that in the compound according to the present invention the functional group (i.e. the functional group with which at least one hydrogen atom of the aromatic group K may be substituted) is a functional groups selected from the group consisting of
- i) —$SO_3M$, wherein M is selected from the group consisting of $H^+$, $Na^+$, $K^+$, $Li^+$, $NH_4^+$, $Ca_2^+$ and $Mg^{2+}$, ii) —OSO₃M, wherein M is selected from the group consisting of H⁺, Na⁺, K⁺, Li⁺, NH₄⁺, Ca²⁺ and Mg²⁺,
iii) —CO₂M, wherein M is selected from the group consisting of H⁺, Na⁺, K⁺, Li⁺, NH₄⁺, Ca²⁺ and Mg²⁺,
iv) an ammonium group selected from the group consisting of —N(CH₃)₄⁺, —N(CH₂CH₃)₄⁺, —N(C₃H₇)₄⁺, —N(C₄H₉)₄⁺, and —N(C₅H₁₁)₄⁺, and
v) an alkyl group selected from the group consisting of —CH₃, —C₂H₅, —C₃H₇, —C₄H₉, —C₅H₁₁, —C₆H₁₃, —C₇H₁₅, —C₈H₁₇, —C₉H₁₉, —C₁₀H₂₁, —C₁₁H₂₃ and —C₁₂H₂₅.

Functional groups i), ii), iii) and iv) are preferred if the compounds according to the present invention are used in water-based compositions, whereas functional group v) (or compounds in which no hydrogen atoms are substituted by any of these functional groups i) to v)) are preferred for compositions that are based on organic solvents.

According to preferred embodiments of the compound according to the present invention 1, 2, 3 or 4 hydrogen atoms, preferably 1 or 2 hydrogen atoms of the heteroaromatic or heteroaromatic group K are substituted by one of the above mentioned functional groups selected from the group consisting of a sulfonic acid group, a sulfuric acid group, an ammonium group and an aliphatic group.

As in the compound according to the present invention two or more hydrogen atoms of the aromatic group K may be substituted by any of the above mentioned functional groups, these groups may be identical or different. However, according to a particularly preferred embodiment of the compound according to the present invention the functional group is —SO₃M, wherein M is selected from the group consisting of H⁺, Na⁺, K⁺, Li⁺, NH₄⁺, Ca²⁺ and Mg²⁺, and if more than one hydrogen atom of the aromatic group K is substituted by a functional group, all these groups are —SO₃M groups, wherein M is selected from the group consisting of H⁺, Na⁺, K⁺, Li⁺, NH₄⁺, Ca²⁺ and Mg²⁺.

According to a first embodiment of the compound according to the present invention K represents a monocyclic aromatic group or a monocyclic heteroaromatic group and the structural subunit Ia' of formula Ia or the structural subunit Ib' of formula Ib

have a general structure selected from the group consisting of general formulae IIa to IIk (for a monocyclic aromatic group K) or from the group consisting of general formula III to IIx (for a monocyclic heteroaromatic group K) (hydrogen atoms in formula IIw and IIx are not shown):

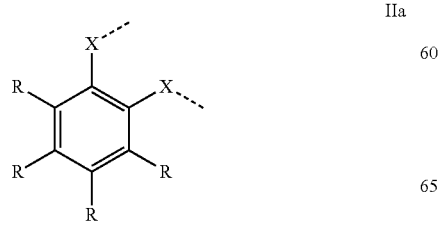

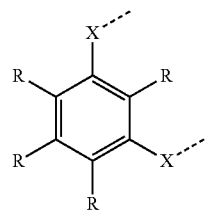

IIb

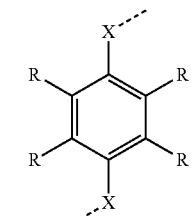

IIc

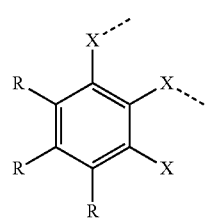

IId

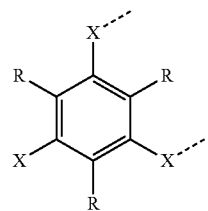

IIe

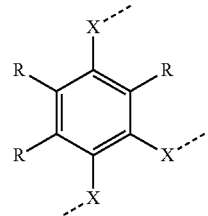

IIf

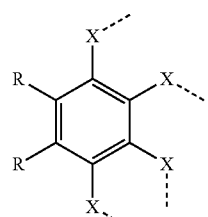

IIg

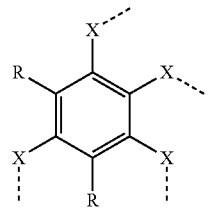

IIh

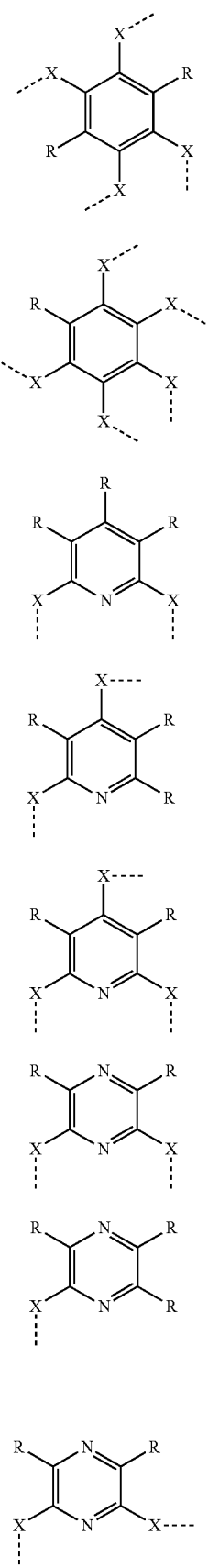

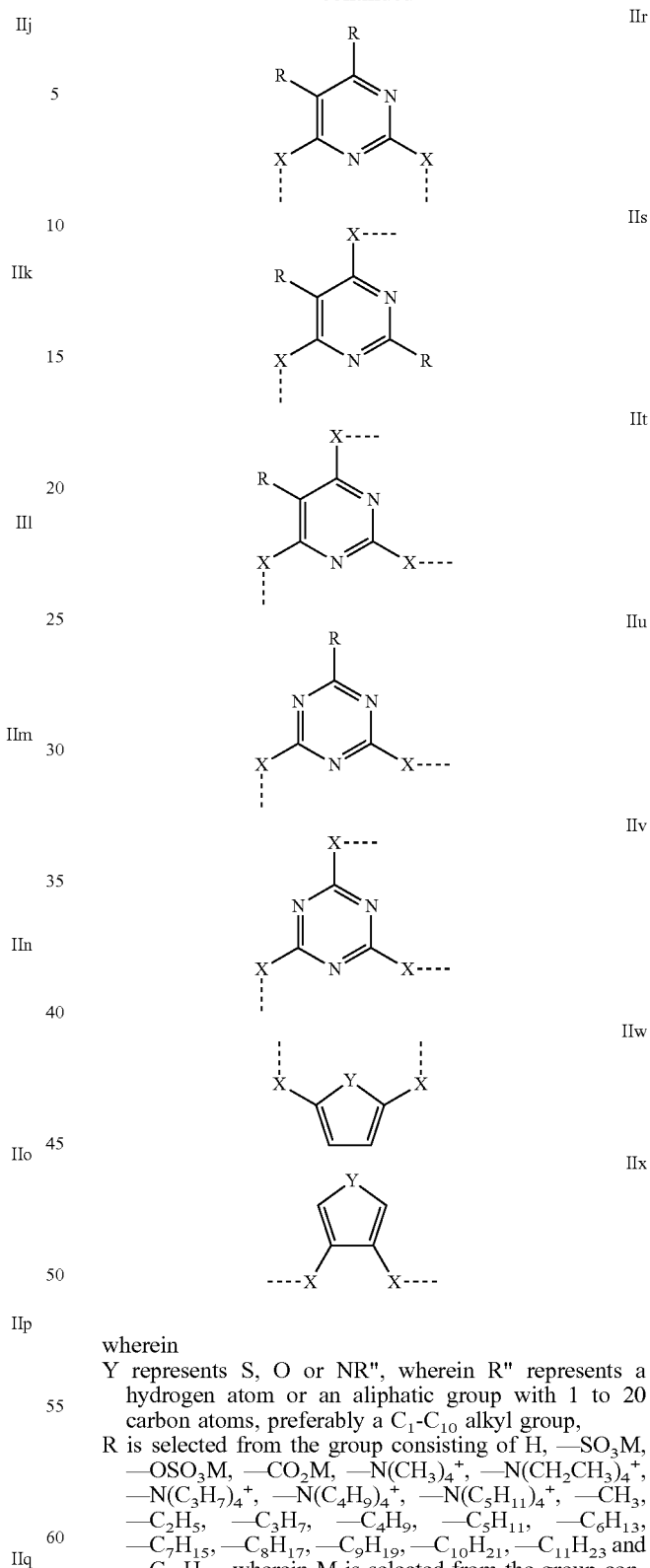

wherein
Y represents S, O or NR'', wherein R'' represents a hydrogen atom or an aliphatic group with 1 to 20 carbon atoms, preferably a $C_1$-$C_{10}$ alkyl group,
R is selected from the group consisting of H, $-SO_3M$, $-OSO_3M$, $-CO_2M$, $-N(CH_3)_4^+$, $-N(CH_2CH_3)_4^+$, $-N(C_3H_7)_4^+$, $-N(C_4H_9)_4^+$, $-N(C_5H_{11})_4^+$, $-CH_3$, $-C_2H_5$, $-C_3H_7$, $-C_4H_9$, $-C_5H_{11}$, $-C_6H_{13}$, $-C_7H_{15}$, $-C_8H_{17}$, $-C_9H_{19}$, $-C_{10}H_{21}$, $-C_{11}H_{23}$ and $-C_{12}H_{25}$, wherein M is selected from the group consisting of $H^+$, $Na^+$, $K^+$, $Li^+$, $NH_4^+$, $Ca^{2+}$ and $Mg^{2+}$,
and wherein the dotted line indicates the bond to A.

From the compounds of the first embodiment according to the present invention particularly preferred compounds are those in which X represents O and in which the following combinations for substituent R per entity K are fulfilled:

n=2, and
R=1×—SO₃M and 3×H or R=2×—SO₃M and 2×H,
or
n=3, and
R=3×H and 3×—SO₃M,
wherein M is selected from the group consisting of H⁺, Na⁺, K⁺, Li⁺, NH₄⁺, Ca²⁺ and Mg²⁺.

According to a second embodiment of the compound according to the present invention K represents a bicyclic aromatic group (i.e. K is based on a naphthalene group) or a bicyclic heteroaromatic group.

According to a first variant of the second embodiment of the compound according to the present invention n represents 2 and the structural subunit Ia' of formula Ia or the structural subunit Ib' of formula Ib

   Ia'

   Ib' have a general structure selected from the group consisting of general formulae IIIa to IIIj (for a bicyclic aromatic group K) or from the group consisting of general formula IIIk to IIIu (for a bicyclic heteroaromatic group K) (hydrogen atoms in formula IIIK to IIIu are not shown):

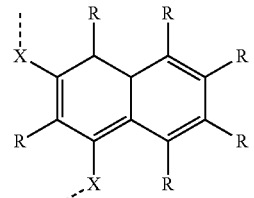   IIIa

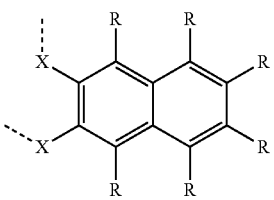   IIIb

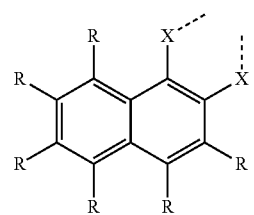   IIIc

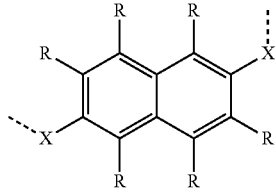   IIId

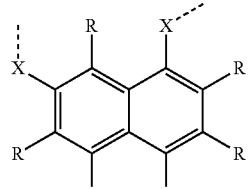   IIIe

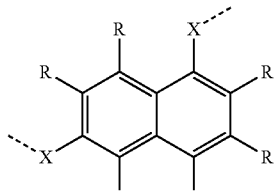   IIIf

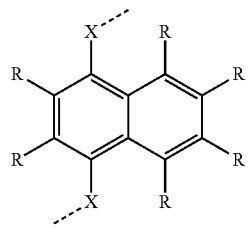   IIIg

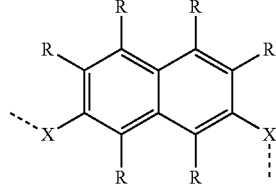   IIIh

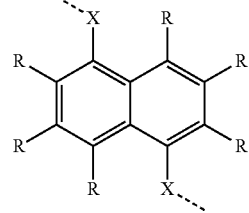   IIIi

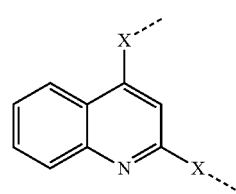   IIIj

IIIk

IIIl 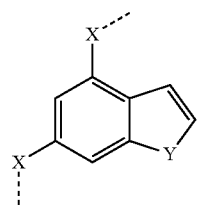

IIIm 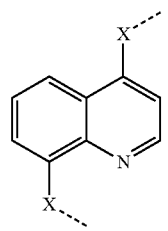

IIIn 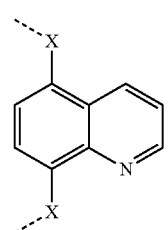

IIIo 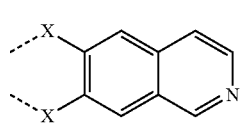

IIIp 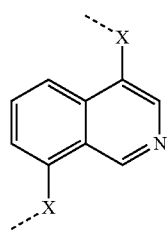

IIIq 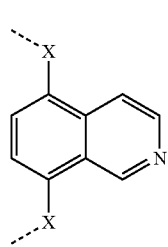

IIIr 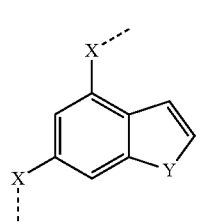

IIIs 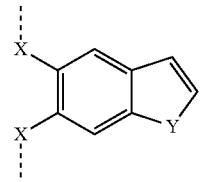

IIIt 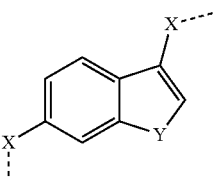

IIIu 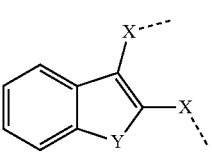

wherein

Y represents S, O or NR", wherein R" represents a hydrogen atom or an aliphatic group with 1 to 20 carbon atoms, preferably a $C_1$-$C_{10}$ alkyl group, R is selected from the group consisting of H, —$SO_3M$, —$OSO_3M$, —$CO_2M$, —$N(CH_3)_4^+$, —$N(CH_2CH_3)_4^+$, —$N(C_3H_7)_4^+$, —$N(C_4H_9)_4^+$, —$N(C_5H_{11})_4^+$, —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —$C_{11}H_{23}$ and —$C_{12}H_{25}$, wherein M is selected from the group consisting of $H^+$, $Na^+$, $K^+$, $Li^+$, $NH_4^+$, $Ca^{2+}$ and $Mg^{2+}$, and wherein the dotted line indicates the bond to A.

In context with this first variant of the second embodiment compounds are particularly preferred in which X represents O and in which the following combinations for substituent R per entity K are fulfilled:

R=2×—$SO_3M$ and 4×H, or

R=3×—$SO_3M$ and 3×H, wherein M is selected from the group consisting of $H^+$, $Na^+$, $K^+$, $Li^+$, $NH_4^+$, $Ca^{2+}$ and $Mg^{2+}$.

According to a second variant of the second embodiment of the compound according to the present invention n represents 3 and the structural subunit Ia' of formula Ia or the structural subunit Ib' of formula Ib $$K \!\!-\!\!\!\left[X\right]_n \quad \text{Ia'}$$

$$K\!\!\left\{\!\!\begin{array}{c}[X]\\ [X]\end{array}\!\!\right\}_m \quad \text{Ib'}$$

have a general structure selected from the group consisting of general formulae IVa to IVl (for a bicyclic aromatic group K) or from the group consisting of general formula IVm and IVn (for a bicyclic heteroaromatic group K) (hydrogen atoms in formula IIIm and IIIn are not shown):

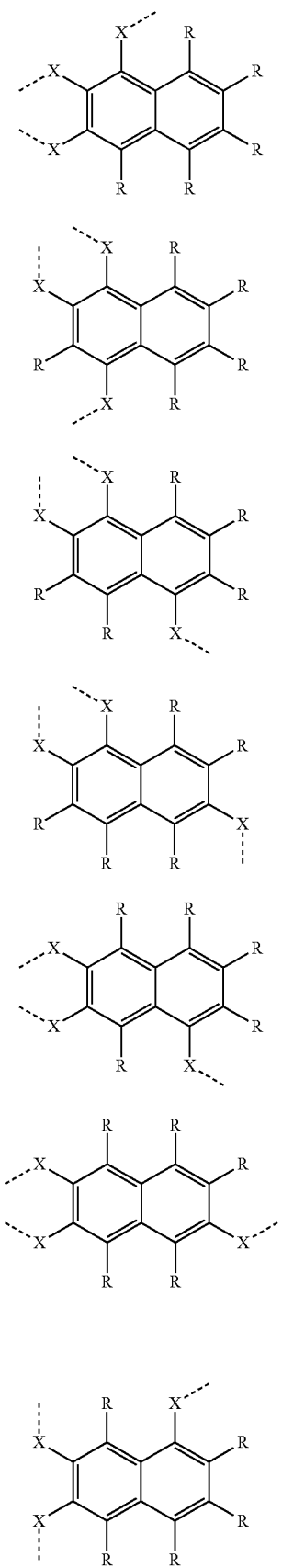
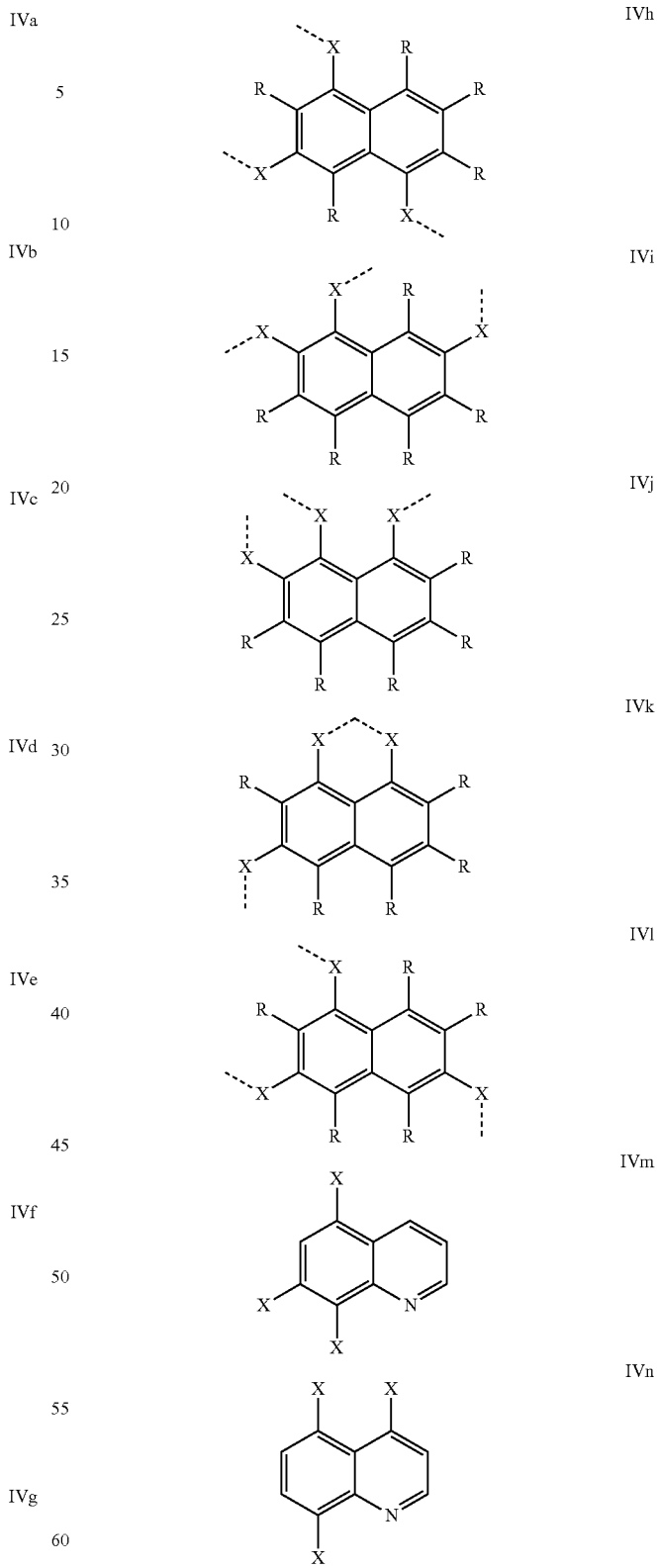
wherein R is selected from the group consisting of H, —SO$_3$M, —OSO$_3$M, —CO$_2$M, —N(CH$_3$)$_4^+$, —N(CH$_2$CH$_3$)$_4^+$, —N(C$_3$H$_7$)$_4^+$, —N(C$_4$H$_9$)$_4^+$, —N(C$_5$H$_{11}$)$_4^+$, —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —C$_{11}$H$_{23}$ and —$C_{12}H_{25}$, wherein M is selected from the group consisting of $H^+$, $Na^+$, $K^+$, $Li^+$, $NH_4^+$, $Ca^{2+}$ and $Mg^{2+}$ and wherein the dotted line indicates the bond to A.

According to a third variant of the second embodiment of the compound according to the present invention n represents 4 and the structural subunit Ia' of formula Ia or the structural subunit Ib' of formula Ib

Ia'

Ib' have a general structure selected from the group consisting of general formulae Va to Vi:

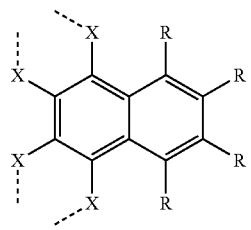

Va

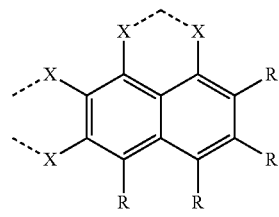

Vb

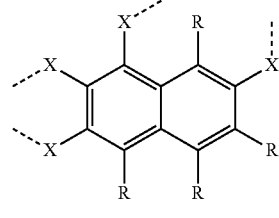

Vc

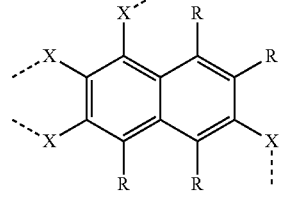

Vd

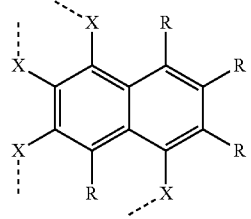

Ve

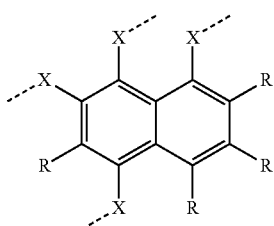

Vf

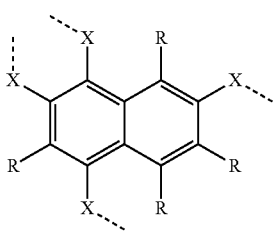

Vg

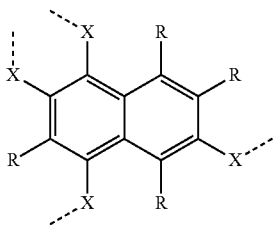

Vh

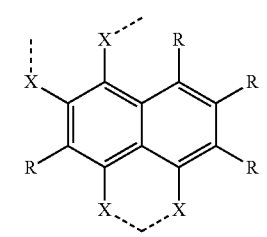

Vi wherein R is selected from the group consisting of H, —$SO_3M$, —$OSO_3M$, —$CO_2M$, —$N(CH_3)_4^+$, —$N(CH_2CH_3)_4^+$, —$N(C_3H_7)_4^+$, —$N(C_4H_9)_4^+$, —$N(C_5H_{11})_4^+$, —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —$C_{11}H_{23}$ and —$C_{12}H_{25}$, wherein M is selected from the group consisting of $H^+$, $Na^+$, $K^+$, $Li^+$, $NH_4^+$, $Ca^{2+}$ and $Mg^{2+}$ and wherein the dotted line indicates the bond to A.

According to a forth variant of the second embodiment of the compound according to the present invention n represents 5 and the structural subunit Ia' of formula Ia or the structural subunit Ib' of formula Ib

Ia'

Ib' have a general structure selected from the group consisting of general formulae VIa to VIe:

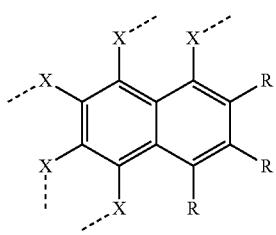

VIa

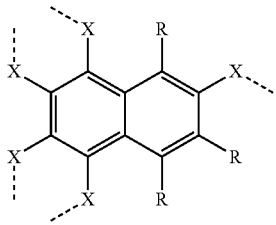

VIb

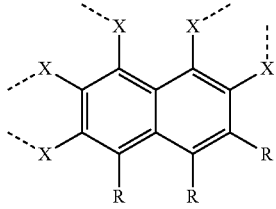

VIc

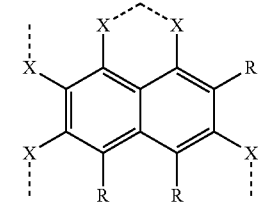

VId

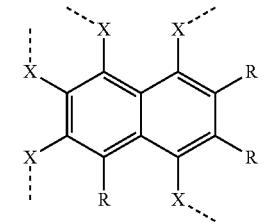

VIe wherein R is selected from the group consisting of H, —$SO_3M$, —$OSO_3M$, —$CO_2M$, —$N(CH_3)_4^+$, —$N(CH_2CH_3)_4^+$, —$N(C_3H_7)_4^+$, —$N(C_4H_9)_4^+$, —$N(C_5H_{11})_4^+$, —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —$C_{11}H_{23}$ and —$C_{12}H_{25}$, wherein M is selected from the group consisting of $H^+$, $Na^+$, $K^+$, $Li^+$, $NH_4^+$, $Ca^{2+}$ and $Mg^{2+}$ and wherein the dotted line indicates the bond to A.

According to a fifth variant of the second embodiment of the compound according to the present invention n represents 6 and the structural subunit Ia' of formula Ia or the structural subunit Ib' of formula Ib $$K\!-\!\!\left[X\right]_n$$  Ia'

Ib' have a general structure selected from the group consisting of general formulae VIIa to VIIj:

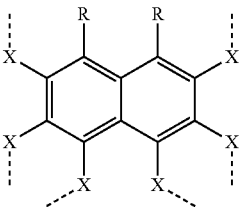

VIIa

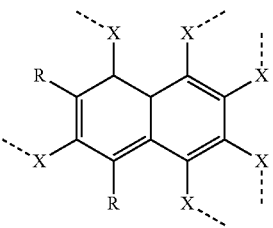

VIIb

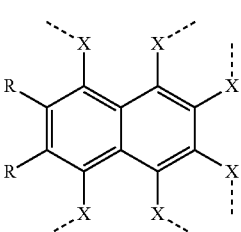

VIIc

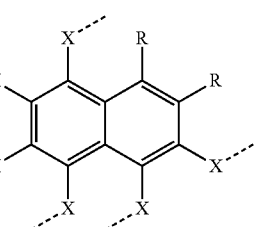

VIId

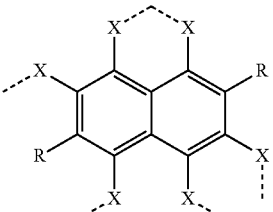

VIIe

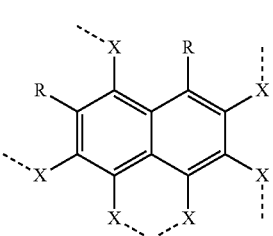

VIIf

VIIg

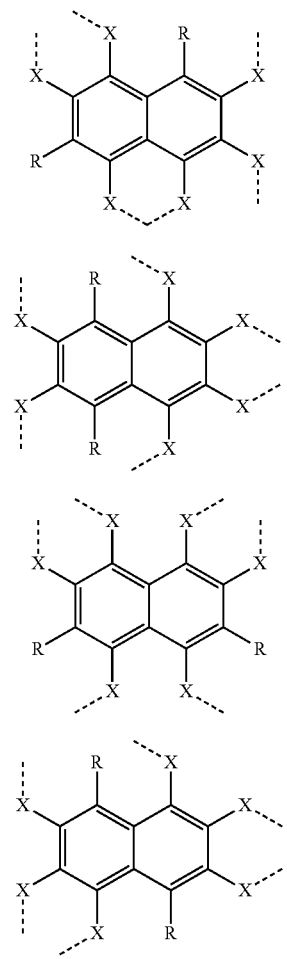

VIIh

VIIi

VIIj wherein R is selected from the group consisting of H, —SO$_3$M, —OSO$_3$M, —CO$_2$M, —N(CH$_3$)$_4$$^+$, —N(CH$_2$CH$_3$)$_4$$^+$, —N(C$_3$H$_7$)$_4$$^+$, —N(C$_4$H$_9$)$_4$$^+$, —N(C$_5$H$_{11}$)$_4$$^+$, —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —C$_{11}$H$_{23}$ and —C$_{12}$H$_{25}$, wherein M is selected from the group consisting of H$^+$, Na$^+$, K$^+$, Li$^+$, NH$_4$$^+$, Ca$^{2+}$ and Mg$^{2+}$ and wherein the dotted line indicates the bond to A.

According to a third embodiment of the compound according to the present invention K represents a tricyclic aromatic group (i.e. K is based on a anthracene group or a phenanthrene group) or a tricyclic heteroaromatic group and the structural subunit Ia' of formula Ia or the structural subunit Ib' of formula Ib Ia'

Ib' have a general structure selected from the group consisting of general formulae VIIIa to VIIIr (for a tricyclic aromatic group K) or have the general formula VIIIs to VIIIu (for a tricyclic heteroaromatic group K) (hydrogen atoms in formula VIIIs, VIIIt and VIIIu are not shown):

VIIIa

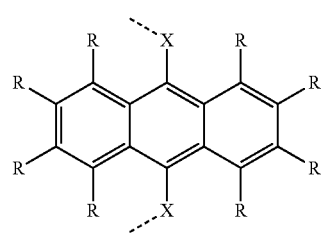

VIIIb

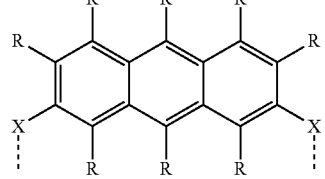

VIIIc

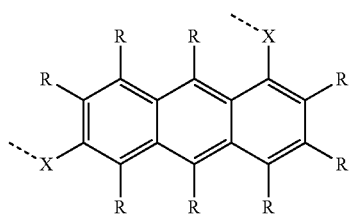

VIIId

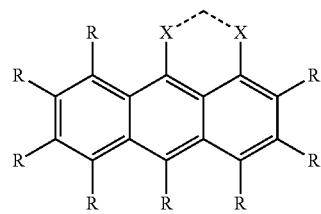

VIIIe

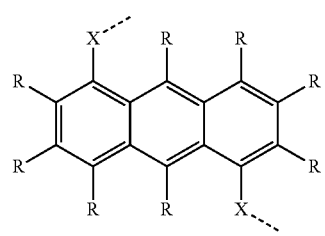

VIIIf

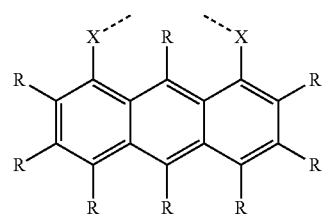

VIIIg

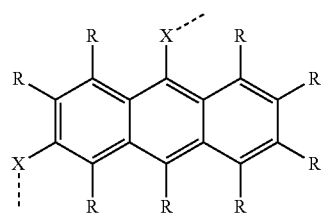

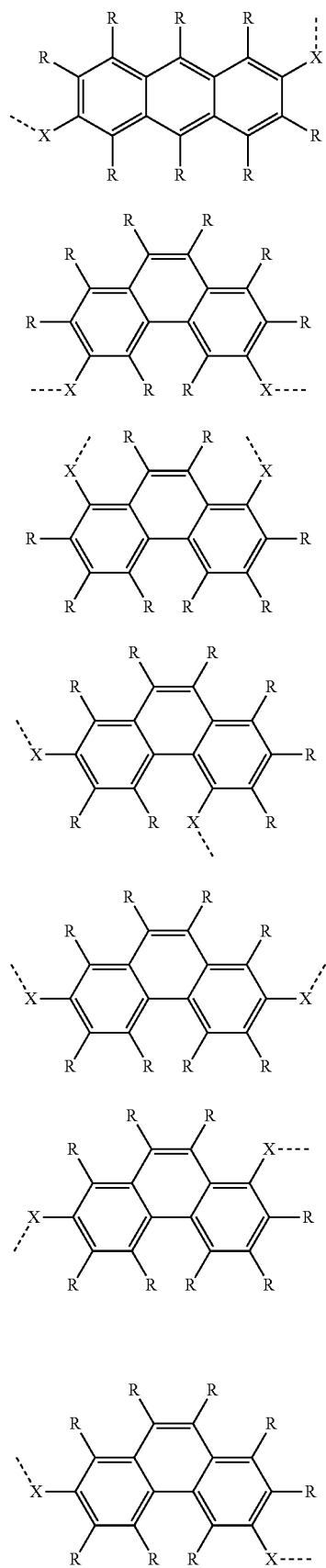
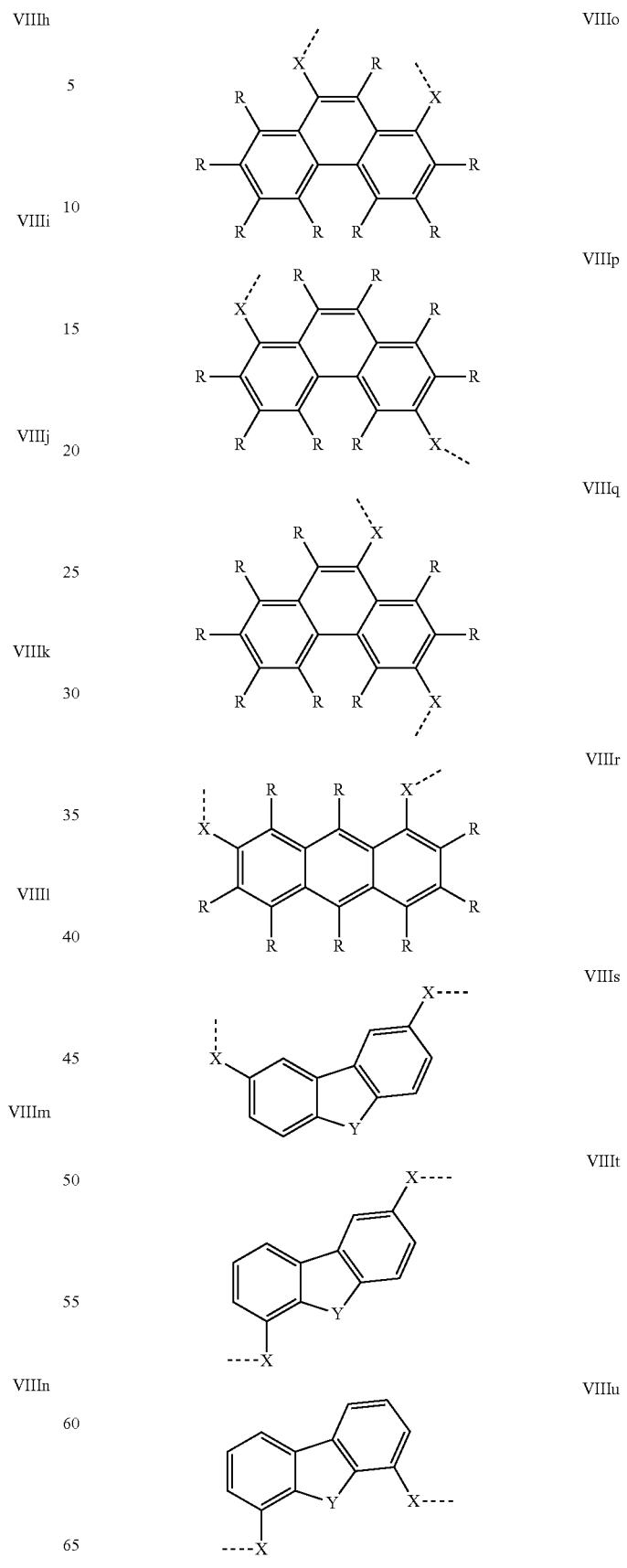

wherein

Y represents S, O or NR″, wherein R″ represents a hydrogen atom or an aliphatic group with 1 to 20 carbon atoms, preferably a $C_1$-$C_{10}$ alkyl group, R is selected from the group consisting of H, —$SO_3M$, —$OSO_3M$, —$CO_2M$, —$N(CH_3)_4^+$, —$N(CH_2CH_3)_4^+$, —$N(C_3H_7)_4^+$, —$N(C_4H_9)_4^+$, —$N(C_5H_{11})_4^+$, —$CH_3$, —$C_2H_5$, —$C_3H_7$, —$C_4H_9$, —$C_5H_{11}$, —$C_7H_{15}$, —$C_8H_{17}$, —$C_9H_{19}$, —$C_{10}H_{21}$, —$C_{11}H_{23}$ and —$C_{12}H_{25}$, wherein M is selected from the group consisting of $H^+$, $Na^+$, $K^+$, $Li^+$, $NH_4^+$, $Ca^{2+}$ and $Mg^{2+}$, and wherein the dotted line indicates the bond to A.

In context with the third embodiment compounds are particularly preferred in which X represents O and in which the following combinations for substituent R per entity K are fulfilled:

R=2×—$SO_3M$ and 6×H, or

R=3×—$SO_3M$ and 5×H, wherein M is selected from the group consisting of $H^+$, $Na^+$, $K^+$, $Li^+$, $NH_4^+$, $Ca^{2+}$ and $Mg^{2+}$ In the compound according to the present invention A represents a fluorinated or perfluorinated aromatic group, more preferably a perfluorinated aromatic group. In this context it is particularly preferred that A has a general structure selected from the group consisting of general formulae IXa to IXo:

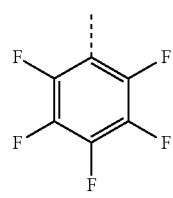
IXa

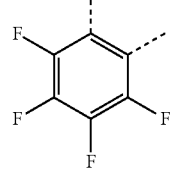
IXb

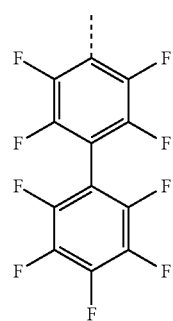
IXc

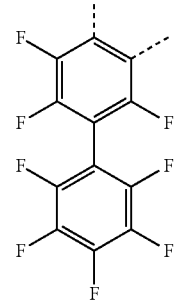
IXd

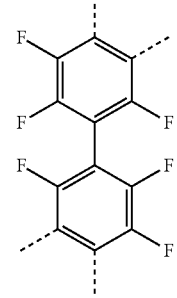
IXe

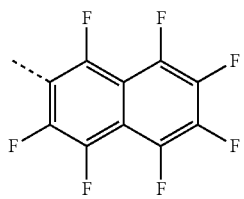
IXf

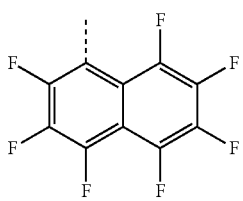
IXg

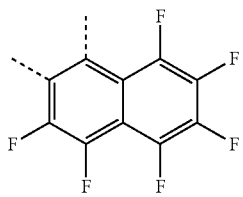
IXh

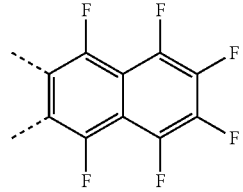
IXi

IXj 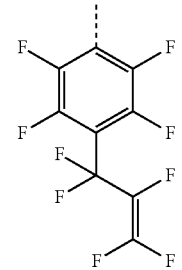
IXk 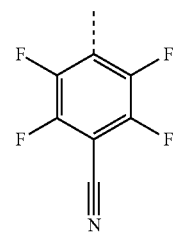
IXl 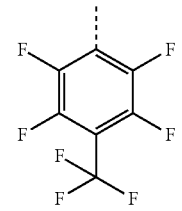
IXm 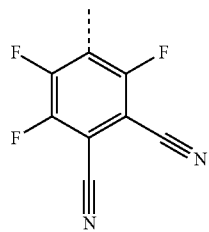
IXn 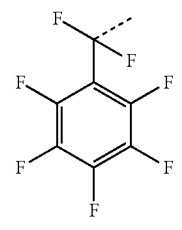
IXo 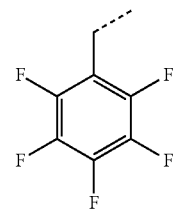
wherein the dotted line indicates the bond to X.
Particularly preferred embodiments of the compound according to the present invention have a general structure selected from the group consisting of general formulae Xa to Xg or the corresponding salts thereof:
Xa 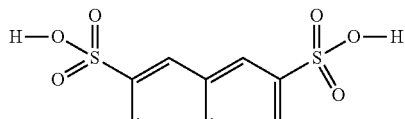
Xb 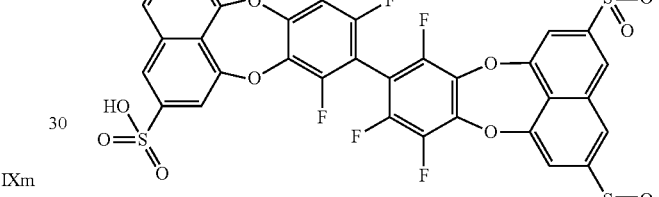
Xc 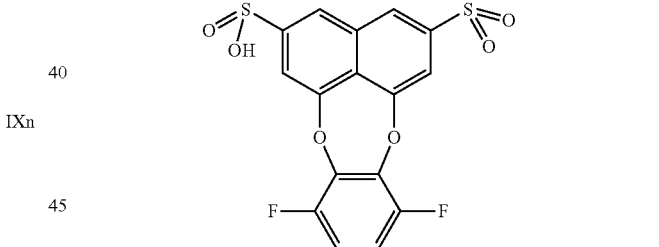
Xd 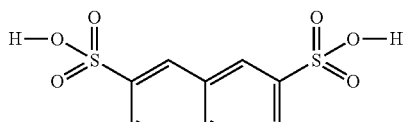

It should be noted that, although in general formulae Xa to Xg the functional groups are shown to be —SO₃H groups, these groups can of course also be partially or completely neutralized and can therefore also be present in the form of —SO₃M groups, in which M is selected from the group consisting of H⁺, Na⁺, K⁺, Li⁺, NH₄⁺, Ca²⁺ and Mg²⁺.

The compound according to the present invention can be prepared in a simply one-step synthesis by reacting the mono- or polycyclic aromatic or heteroaromatic system K in which at least one hydrogen atom may be substituted by the above mentioned functional groups and in which at the position at which X is attached the corresponding acid form —XH is present, i.e.
- a group —OH in case of X=O,
- a group —SH in case of X=S,
- a group —SO₂H in case of X=SO₂, or
- a group —NR'H in case of X=NR', with a fluorinated or perfluorinated aromatic compound, preferably with a perfluorinated aromatic compound having a general structure selected from the group consisting of general formulae XIa to XIh:

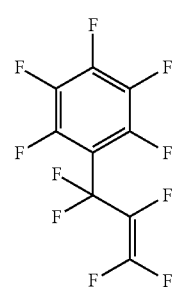

XIg

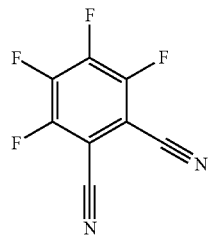

XIh in a nucleophilic aromatic substitution reaction, preferably in the presence of a suitable catalyst. Catalysts that can be used for this purpose can be selected from the group consisting of lithium, potassium, lithium hydride, sodium hydride, lithium t-butoxide, sodium t-butoxide, potassium t-butoxide, lithium-diisopropylamide, n-butyllithium, s-butyllithium, t-butyllithium, lithium hexamethyldisilazide, sodium hexamethyldisilazide, potassium hexamethyldisilazide, lithium hydroxide, sodium hydroxide, potassium hydroxide, barium hydroxide, barium oxide, lithium carbonate, sodium carbonate, potassium carbonate, cesium carbonate, calcium carbonate, sodium hydrogen carbonate, triethylamine, diisopropylethylamine, tetramethylethylenediamine, triethylenediamine, pyridine, dimethylaminopyridine, imidazole and the like, and dehydration condensing agents such as hydrochloric acid, sulfuric acid, diphosphorus pentaoxide, aluminum (III) chloride, boron trifluoride diethyl ether complex, ethyl aluminum dichloride, diethyl aluminum chloride and the like. Preferred catalysts are selected from the group consisting of sodium hydroxide, sodium carbonate and potassium carbonate.

The reaction can be performed in any solvent in which the educts (i.e. the mono- or polycyclic aromatic or heteroaromatic system K in which at the position at which X is attached the corresponding acid form —XH is used and the fluorinated or perfluorinated aromatic compound) can be dissolved or dispersed. Preferably an aprotic polar organic solvent is used, which is preferably selected from the group consisting N,N-dimethylformamide, N,N-dimethylacetamide, N-methylpyrrolidone, 1,3-dimethyl-2-imidazolidinone, dimethylsulfoxide, tetrahydrofuran and dioxane.

The possible reaction temperature generally ranges from 50° C. to the boiling point of a solvent used and is preferably within a range of 0 to 140° C. The reaction time is usually at 0.1 to 100 hours. After completion of the reaction, purification can be made by distilling off of the reaction solvent, protonation of the sulfonate by means of a cationic exchange resins, extraction operations with a solvent such as methanol or the like, or by precipitation.

A contribution towards solving the above mentioned objects is also made by a composition comprising
I) at least one conductive polymer,
II) at least one solvent and
III) at least one compound according to the present invention,
wherein the composition preferably is a dispersion or a solution, particularly preferred dispersion.

Conductive polymers I) are understood here to mean especially the compound class of the conjugated polymers which, after oxidation or reduction, possess electrical conductivity. Preferably, such conjugated polymers are considered to be conductive polymers which, after oxidation, possess an electrical conductivity in the order of magnitude of at least $0.01\ \mu S\ cm^{-1}$.

The conductive polymer I) in the composition according to the present invention preferably comprises, as a conjugated polymer, at least one polythiophene, polypyrrole or polyaniline, which are optionally substituted.

More preferably, the conductive polymer I) comprises at least one polythiophene with repeat units of the general formula (A) or of the general formula (B) or a combination of units of the general formulas (A) and (B), preferably a polythiophene with repeating units of the general formula (B):

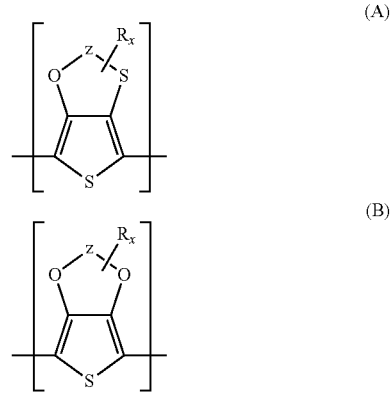

wherein
z stands for an optionally substituted $C_1$-$C_5$-alkylene radical,
R stands for a linear or branched, optionally substituted $C_1$-$C_{18}$-alkyl radical, an optionally substituted $C_5$-$C_{12}$-cycloalkyl radical, an optionally substituted $C_6$-$C_{14}$-aryl radical, an optionally substituted $C_7$-$C_{18}$-aralkyl radical, an optionally substituted $C_1$-$C_4$-hydroxyalkyl radical or a hydroxyl radical,
x stands for a whole number from 0 to 8 and
in the case where multiple radicals R are connected to Y, these can be identical or different.

The general formulas (A) and (B) are to be so understood, that x substituents R can be connected to alkylene radical Y.

Particularly preferred are polythiophenes with repeating units of the general formula (B), wherein z stands for an optionally substituted $C_2$-$C_3$-alkylene radical and x stands for 0 or 1. Especially preferred as polythiophene is poly(3,4-ethylenedioxythiophene), which is optionally substituted.

In the context of the invention, the prefix poly- is to be understood as meaning that more than one identical or different repeating units of the general formulas (A) and/or (B) are contained in the polymer or polythiophene. As well as the repeating units of the general formulas (A) and/or (B), the polythiophene can also comprise other repeating units, it being preferred that at least 50%, particularly preferred that at least 75% and most preferred that at least 95% of all repeating units of the polythiophene exhibit the general formula(s) (A) and/or (B), preferably the general formula (B). The polythiophenes contain in total n repeating units of the general formula(s) (A) and/or (B), preferably of the general formula (B), n being a whole number from 2 to 2000, preferably from 2 to 100. The repeating units of the general formula(s) (A) and/or (B), preferably of the general formula (B), within a polythiophene can each be identical or different. Polythiophenes with identical repeating units of the general formula (B) are preferred.

The polythiophenes preferably carry H on the end groups.

In the context of the invention, $C_1$-$C_5$-alkylene radicals z are preferably methylene, ethylene, n-propylene, n-butylene or n-pentylene. $C_1$-$C_{18}$-Alkyl R is preferably linear or branched $C_1$-$C_{18}$-alkyl radicals such as methyl, ethyl, n- or isopropyl, n-, iso-, sec- or tert-butyl, n-pentyl, 1-methylbutyl, 2-methylbutyl, 3-methylbutyl, 1-ethylpropyl, 1,1-dimethylpropyl, 1,2-dimethylpropyl, 2,2-dimethylpropyl, n-hexyl, n-heptyl, n-octyl, 2-ethylhexyl, n-nonyl, n-decyl, n-undecyl, n-dodecyl, n-tridecyl, n-tetradecyl, n-hexadecyl or n-octadecyl, $C_5$-$C_{12}$-cycloalkyl radicals R are, for example, cyclopentyl, cyclohexyl, cycloheptyl, cyclooctyl, cyclononyl or cyclodecyl, $C_6$-$C_{14}$-aryl radicals R are, for example, phenyl or naphthyl, and $C_7$-$C_{18}$-aralkyl radicals R are, for example, benzyl, o-, m-, p-tolyl, 2,3-, 2,4-, 2,5-, 2,6-, 3,4-, 3,5-xylyl or mesityl. The above list serves to illustrate the invention by way of example and should not be considered to be exclusive.

In the context of the invention, any further substituents of the z radicals and/or of the R radicals include numerous organic groups, for example alkyl, cycloalkyl, aryl, aralkyl, alkoxy, halogen, ether, thioether, disulfide, sulfoxide, sulfone, sulfonate, amino, aldehyde, keto, carboxylic ester, carboxylic acid, carbonate, carboxylate, cyano, alkylsilane and alkoxysilane groups, and also carboxamide groups.

Possible substituents for polyaniline or polypyrrole include, for example, the z and R radicals listed above and/or the further substituents of the z and R radicals. Preference is given to unsubstituted polyanilines.

The polythiophenes that are comprised in the conductive polymer I) may be uncharged or cationic. In preferred embodiments, they are cationic, "cationic" relating only to the charges which reside on the main polythiophene chain. According to the substituent on the R radicals, the polythiophenes may bear positive and negative charges in the structural unit, in which case the positive charges are on the main polythiophene chain and the negative charges are, if present, on the R radicals substituted by sulfonate or carboxylate groups. The positive charges of the main polythiophene chain may be partly or fully saturated by the anionic groups which may be present on the R radicals. Viewed overall, the polythiophenes in these cases may be cationic, uncharged or even anionic. Nevertheless, in the context of the invention, all are considered to be cationic polythiophenes, since the positive charges on the main polythiophene chain are crucial. The positive charges are not shown in the formulae, since their exact number and position cannot be stated unambiguously. The number of positive charges is, however, at least 1 and at most n, where n is the total number of all repeat units (identical or different) within the polythiophene.

To balance the positive charge, if this has not already been done by the optionally sulfonate- or carboxylate-substituted and thus negatively charged R radicals, the cationic polythiophenes require anions as counterions. Counterions may be monomeric or polymeric anions, the latter also being referred to hereinafter as polyanions.

Polymeric anions are preferred over monomeric anions, since they contribute to film formation and, owing to their size, lead to thermally more stable, electrically conductive films. Polymeric anions here may, for example, be anions of polymeric carboxylic acids, such as polyacrylic acids, polymethacrylic acid or polymaleic acids, or polymeric sulfonic acids, such as polystyrenesulfonic acids and polyvinylsulfonic acids. These polycarboxylic and -sulfonic acids may also be copolymers of vinylcarboxylic and vinylsulfonic acids with other polymerizable monomers, such as acrylic esters and styrene. Other preferred copolymers are block-copolymers of polystyrenesulfonic acid, polyalkylstyrenes and (hydrogenated) isoprenes/dienes.

A preferred polyanion is an anion of a polymeric carboxylic or sulfonic acid. A particularly preferred polyanion is the anion of polystyrenesulfonic acid (PSS). The molecular weight of the polyacids which afford the polyanions is preferably 1000 to 2 000 000, more preferably 2000 to 500 000. The polyacids or alkali metal salts thereof are commercially available, for example polystyrenesulfonic acids and polyacrylic acids, or else are preparable by known processes (see, for example, Houben Weyl, Methoden der organischen Chemie [Methods of Organic Chemistry], vol. E 20 Makromolekulare Stoffe [Macromolecular Substances], part 2, (1987), p. 1141 ff.).

Polyanions and conjugated polymer (i.e. polythiophene, polypyrrole or polyaniline, which are optionally substituted) may be present in the composition according to the present invention especially in a weight ratio of 0.5:1 to 50:1, preferably of 1:1 to 30:1, more preferably 2:1 to 20:1. The weight of the conjugated polymer corresponds here to the initial weight of the monomers used, assuming that there is full conversion in the polymerization.

The monomeric anions used are, for example, those of $C_1$-$C_{20}$-alkanesulfonic acids, such as those of methanesulfonic acid, ethanesulfonic acid, propanesulfonic acid, butanesulfonic acid or higher sulfonic acids such as dodecanesulfonic acid, of aliphatic perfluorosulfonic acids, such as trifluoromethanesulfonic acid, perfluorobutanesulfonic acid or perfluorooctanesulfonic acid, of aliphatic $C_1$-$C_{20}$-carboxylic acids such as 2-ethylhexylcarboxylic acid, of aliphatic perfluorocarboxylic acids, such as trifluoroacetic acid or perfluorooctanoic acid, and aromatic sulfonic acids optionally substituted by $C_1$-$C_{20}$-alkyl groups, such as benzenesulfonic acid, o-toluenesulfonic acid, p-toluenesulfonic acid or dodecylbenzenesulfonic acid, and of cycloalkanesulfonic acids such as camphorsulfonic acid, or tetrafluoroborates, hexafluorophosphates, perchlorates, hexafluoroantimonates, hexafluoroarsenates or hexachloroantimonates. Preferred monomeric anions are the anions of p-toluenesulfonic acid, methanesulfonic acid or camphorsulfonic acid.

Cationic polythiophenes which contain anions as counterions to balance the charge are often also referred to in the technical field as polythiophene/(poly)anion complexes. It is therefore particularly preferred that in the composition according to the present invention the conductive polymer I) comprises a complex of a polythiophene and mono- or a polyanion or a combination of both, preferably a complex of poly(3,4-ethylenedioxythiophene) (PEDOT) and polystyrenesulfonic acid (PSS), also referred to as a "PEDOT/PSS"-complex. Such complexes can be obtained if the monomers used to prepare the polythiophene (like 3,4-ethylenedioxythiophene) are oxidatively polymerized in the presence of the polyanions in suitable solvents like water, as disclosed, for example, in EP 0 440 957 A2. The complexes of polythiophenes and polyanions, in particular the PEDOT/

PSS-complexes, are preferably present in the composition according to the present invention in the form of particles.

As a further component the composition according to the present invention also comprises at least one solvent II). Preferred solvents are water, organic solvents selected from the group consisting of aliphatic hydrocarbons, such as heptane, hexane, pentane, octane, terpenes or petroleum ether, aromatic hydrocarbons such as benzene, toluene, xylene, mesitylene, biphenyl, ethers, such as diethylether, diisopropylether, methyltert-butylether dibutylether, diphenylether, anisole and ethylenglycol ethers such as polyethylenglycol (PEG), ethylene glycol monomethyl ether, ethylene glycol monoethyl ether, ethylene glycol monobutyl ether, ethylene glycol monophenyl ether, diethylene glycol monomethyl ether, diethylene glycol monoethyl ether, ethylene glycol dimethyl ether, ethylene glycol diethyl ether, propylen glycol monopropyl ether, dipropylen glycol monomethylether, dipropylen glycol dimethylether, diethylene glycol monomethyl ether or ethylene glycol dibutyl ether, esters such as methylacetate, ethylacetate, propylacetate or butylacetate, methylbenzoate, ethylbenzoate, propylbenzoate, butylbenzoate, γ-butyrolactone, δ-valerolactone, γ-valerolactone, ethylene glycol methyl ether acetate, ethylene glycol monoethyl ether acetate, ethylene glycol monobutyl ether acetate, propylene glycol methyl ether acetate, halogenated hydrocarbons such as dichloromethane, dichloroethane, chlorobenzene, chloroform, tetrachloromethane, trichloroethane or trichloroethene, aliphatic nitriles such as acetonitrile, aliphatic sulphoxides and sulphones such as dimethylsulfoxide or sulfolane, aliphatic carboxylic acids such as acetic acid, aliphatic carboxylic acid amides such as acetamide, dimethyl acetamide or dimethylformamide and ketones such as acetone or methyl-t-butyl ketone, alcohols such as methanol, ethanol, propanol, butanol, hexanol, terpineol, 1,2-propandiol, ethylenglycol or dodecanol, acetals such as glyme (dimethoxyethane), diglyme, tetraglyme, or dioxolane, carbonates such as propylene carbonate or ethylene carbonate and other solvent classes like oligo- or polysiloxanes, and mixtures of at least two of these solvents.

As component III) the composition according to the present invention comprises at least one compound according to the present invention, wherein it is preferred that the composition according to the present invention comprises the at least one compound III) in an amount of 0.01 to 10 wt.-%, preferably 0.1 to 7.5 wt.-% and most preferably 0.5 to 5 wt.-%, in each case based on the total weight of the composition. The weight ratio of the at least one compound III) and the conductive polymer I) (in case of a polythiophene/(poly)anion complex the weight ratio of the at least one compound III) and the total weight of polythiophene and polyanion) is preferably in the range from 1:100 to 100:1, more preferably in the range from 1:10 to 10:1 and most preferably in the range from 1:5 to 5:1.

Besides at least one conductive polymer I), at least one solvent II) and at least one compound according to the present invention III) the composition according to the present invention may comprise further additives IV) being different from components I), II) and III), such as surface-active substances, e.g. anionic surfactants, such as e.g. alkylbenzenesulphonic acids and salts, paraffinsulphonates, alcohol sulphonates, ether sulphonates, sulphosuccinates, phosphate esters, alkyl ether carboxylic acids or carboxylates, cationic surfactants, such as e.g. quaternary alkylammonium salts, nonionic surfactants, such as e.g. linear alcohol ethoxylates, oxo alcohol ethoxylates, alkylphenol ethoxylates or alkyl polyglucosides, adhesion promoters, such as e.g. organofunctional silanes or hydrolysates thereof, e.g. 3-glycidoxypropyltrialkoxysilane, 3-aminopropyltriethoxysilane, 3-mercaptopropyltrimethoxysilane, 3-methacryloxypropyltrimethoxysilane, vinyltrimethoxysilane or octyltriethoxysilane, or crosslinking agents, such as melamine compounds, masked isocyanates, functional silanes—e.g. tetraethoxysilane, alkoxysilane hydrolysates, e.g. based on tetraethoxysilane, epoxysilanes, such as 3-glycidoxypropyltrialkoxysilane, epoxides or oxetanes, amines, quaternary amines, polyamines or quaternary polyamines, binders, such as, for example, polyalkylene glycols, polyacrylates, polyurethanes, polyesters, polyethers, polyamides or polyvinyl alcohol, or additives which increase the conductivity, such as, for example, polyalkylene glycols, in particular polyethylene glycols or polypropylene glycols, polyglycerols or mixtures of these, polyols, such as propylene glycol and ethylene glycol, sulphoxides, such as dimethylsulphoxide, carboxylic acid amides, such as methylacetamide, dimethylacetamide, dimethylformamide, N-methylpyrrolidone, N-cyclohexylpyrrolidone, ionic liquids, sugars, such as sorbitol.

The amount of these additives will of course depend on the nature of the additive, but is usually in the range from 0 to 20 wt.-%, more preferably from 1 to 15 wt.-% and most preferably from 2.5 to 10 wt.-%, based on the total weight of the composition.

Preferably, the composition according to the present invention comprises, in each case based on the total weight of the composition, I) 0.01 to 10 wt.-%, more preferably 0.1 to 7.5 wt.-% and most preferably 0.5 to 5 wt.-%, of the conductive polymer;

III) 0.01 to 10 wt.-%, more preferably 0.1 to 7.5 wt.-% and most preferably 0.2 to 5 wt.-%, of the at least one compound according to the present invention;

IV) 0 to 20 wt.-%, more preferably from 1 to 15 wt.-% and most preferably from 2.5 to 10 wt.-%, of further additives IV) being different from components I), II) and III), wherein the reminder is the solvent II).

It is furthermore preferable for the composition according to the present invention to have a pH in a range of from 1 to 12, particularly preferably in a range of from 4 to 8, at a temperature of 25° C. The viscosity at 20° C. of the composition according to the present invention is preferably less than 1,000 mPas, preferably less than 400 mPas.

The solids content of the composition according to the present invention is preferably in a range of from 0.1 to 10 wt. %, particularly preferably in a range of from 0.5 to 7.5 wt. % and most preferably in a range of from 1 to 5 wt. %.

The composition according to the present invention can be obtained by various processes.

According to a first embodiment, the composition according to the present invention can be obtained by oxidatively polymerizing the monomers used to prepare the conductive polymer I), such as 3,4-ethylenedioxythiophene, in the presence of the compound according to the present invention III) in an appropriate solvent. The solvent used for the polymerization reaction can be the solvent II) that is present in the composition according to the present invention, however, it is also possible to substitute the solvent used for the polymerization reaction by a different solvent (such a process is disclosed, for example, in U.S. Pat. No. 6,692,662 B2) or to add a further solvent to the solvent used for the polymerisation reaction to obtain a solvent mixture.

According to a second (and preferred) embodiment, the composition according to the present invention can be obtained by simply adding the compound according to the present invention III) to a composition that already comprises the conductive polymer I), preferably to an aqueous PEDOT/PSS-dispersion. In this case it is also possible that the solvent used for the polymerization reaction can be the solvent II) that is present in the composition according to the present invention or that the solvent used for the polymerization reaction is substituted by a different solvent as disclosed, for example, in U.S. Pat. No. 6,692,662 B2 or that a further solvent is added to the solvent used for the polymerization reaction to obtain a solvent mixture.

If necessary, the mixture of components I), II) and III) obtained by one of the above mentioned processes is heated until all the components are dissolved, wherein the maximum temperature will of course depend on the boiling point of the solvent that is used.

A contribution towards solving the above mentioned objects is also made by a process for the preparation of a conductive layer, comprises the process steps:

(P1) superimposing a substrate with the composition according to the present invention
or
first superimposing a substrate with a composition comprising the solvent and the compound according to the present invention (but not necessarily comprising the conductive polymer), at least partial removal of the solvent and then superimposing the substrate with a composition according to the present invention or with a composition comprising the solvent and the conductive polymer (but not necessarily comprising the compound according to the present invention);
or
first superimposing a substrate with a composition comprising the solvent and the conductive polymer (but not necessarily comprising the compound according to the present invention), at least partial removal of the solvent and then superimposing the substrate with the composition according to the present invention or with a composition comprising the solvent the compound according to the present invention (but not necessarily comprising a conductive polymer);
(P2) at least partial removal of the solvent.

In process step (P1) a substrate is superimposed with the composition according to the present invention (or with a composition comprising the solvent and either the conductive polymer I) or the compound according to the present invention III)). All layers which can be employed in electronic components, such as, for example, in an OLED, are suitable as the substrate. Thus, in particular, the substrate can be one which is furnished with a preferably transparent base electrode, the substrate itself preferably also being transparent. Glass, PET or other transparent plastics, for example, can be employed as transparent substrate, onto which a transparent electrically conductive electrode is then introduced, such as e.g. an electrode made of indium-tin oxide (ITO), doped zinc- or tin oxide or a conductive polymer. Particularly suitable transparent plastic substrates are, for example, polycarbonates, polyesters, such as e.g. PET and PEN (polyethyleneterephthalate and polyethylenenaphthalinedicarboxylate), copolycarbonates, polyacrylates, polysulphones, polyethersulphones (PES), polyimides, polyethylene, polypropylene, cyclic polyolefins or cyclic olefin copolymers (COC), hydrated styrene polymers or hydrated styrene copolymers. Suitable polymer bases can, for example, also be films such as polyester films, PES films from the Sumitomo company or polycarbonate films from the Bayer AG company (Makrofol®). According to the invention, ITO coated glass is particularly preferred as substrate.

Superimposing the substrate with the composition according to the present invention or with a composition comprising the solvent and either the conductive polymer or the compound according to the present invention can then be accomplished by known methods, for example by spin coating, dipping, pouring, dropping on, injecting, spraying, knife application, spreading or printing, for example inkjet, screen, intaglio, offset or pad printing, in a wet film thickness of 0.1 µm to 250 µm, preferably in a wet film thickness of 0.5 µm to 50 µm, and then dried at a temperature of 20° C. to 200° C.

In process step (P2) the solvent that is contained in the composition that has been applied is then at least partially removed to obtain an electrically conductive layer comprising the conductive polymer I) and the compound according to the present invention III), said removal preferably being performed by simple evaporation.

According to a particularly preferred embodiment of the process according to the present invention process steps (P1) and (P2) are is just two steps in the manufacture of an OLED. As stated above, an OLED usually comprises
an anode
a hole injection layer
an emitter layer and
a cathode,
wherein the hole injection layer is preferably prepared by the process according to the present invention. The OLED may comprise further layers, such as an electron injection layer that is located between the electroluminescence layer and the cathode.

The OLED the hole injection layer of which has been prepared using the composition according to the present invention can, for example, exhibit any of the following layer structures (a) to (h):
  (a) anode/
    hole injection layer/
    at least one emitter layer/
    cathode;
  (b) anode/
    hole injection layer/
    hole transport layer/
    at least one emitter layer/
    cathode;
  (c) anode/
    hole injection layer/
    at least one emitter layer/ electron injection layer/
cathode;
(d) anode/
hole injection layer/
hole transport layer/
at least one emitter layer/
electron injection layer/
cathode;
(e) anode/
hole injection layer/
at least one emitter layer/
electron transport layer/
cathode;
(f) anode/
hole injection layer/
hole transport layer/
cathode;
at least one emitter layer/
electron transport layer/
cathode;
(g) anode/
hole injection layer/
at least one emitter layer/
electron transport layer/
electron injection layer/
cathode;
(h) anode/
hole injection layer/
hole transport layer/
at least one emitter layer/
electron transport layer/
electron injection layer/
cathode.

The layer structures (a) to (h) can be embodied either with the anode located next to the substrate, the substrate being, for example, glass or a transparent plastic film, or with the cathode located next to the substrate.

The anode layer is preferably based on indium tin oxide, indium zinc oxide, fluorine-doped tin oxide, tungsten trioxide, titanium dioxide, molybdenum trioxide, aluminium zinc oxide, gallium indium zinc oxide, aluminium, silver, palladium, copper, gold, platinum, and alloys thereof, for example silver-palladium-copper and molybdenum-chrome.

Suitable materials for the emitter layer are conjugated polymers such as polyphenylenevinylenes and/or polyfluorenes, for example, the polyparaphenylenevinylene derivatives and polyfluorene derivatives described in WO-A-90/13148, or emitters from the class of low molecular emitters, also termed "small molecules" in technical circles, such as aluminium complexes, such as, for example, tris(8-hydroxyquinolinato)aluminium ($Alq_3$), fluorescence dyes, e.g. quinacridones, or phosphorescent emitters such as, for example, $Ir(ppy)_3$. Further suitable materials for the emitter layer are described e.g. in DE-A-196 27 071. Particularly preferred as emitter layer, according to the invention, is tris(8-hydroxyquinolinato)aluminium ($Alq_3$).

Preferred as the injection layer are single Ca layers or a stack structure consisting of a Ca layer and another layer, which consists of one or more materials selected from the group IA and IIA metals of the periodic table, excluding Ca, which exhibit a work function from 1.5 to 3.0 eV, and oxides, halogenides and carbonates thereof. Examples of group IA metals of the periodic table which exhibit a work function from 1.5 to 3.0 eV, and oxides, halogenides and carbonates thereof, are lithium, lithium fluoride, sodium oxide, lithium oxide and lithium carbonate. Examples of group IIA metals of the periodic table, excluding Ca, which exhibit a work function from 1.5 to 3.0 eV, and oxides, halogenides and carbonates thereof, are strontium, magnesium oxide, magnesium fluoride, strontium fluoride, barium fluoride, strontium oxide and magnesium carbonate.

The electron transport layer can consist of materials such as, for example, oxadiazol derivatives, anthraquinodimethane or derivatives thereof, benzoquinone or derivatives thereof, naphthoquinone or derivatives thereof, anthraquinone or derivatives thereof, tetracyanoanthraquinodimethane or derivatives thereof, fluorenone derivatives, diphenyldicyanoethylene or derivatives thereof, diphenoquinone derivatives and metal complexes of 8-hydroxyquinoline or derivatives thereof, polyquinoline or derivatives thereof, polyquinoxaline or derivatives thereof or polyfluorene or derivatives thereof.

Particularly suitable materials for the cathode layer are transparent or translucent materials with a relatively low work function (preferably lower than 4.0 eV). Examples of this type of material are metals, such as lithium (Li), sodium (Na), potassium (K), rubidium (Rb), caesium (Cs), Be, magnesium (Mg), calcium (Ca), strontium (Sr), barium (Ba), aluminium (Al), scandium (Sc), vanadium (V), Zn, yttrium (Y), indium (In), cerium (Ce), samarium (Sm), Eu, Tb and ytterbium (Yb); alloys consisting of two or more of these metals; alloys consisting of one or more of these metals and one or more metals selected from Au, Ag, Pt, Cu, manganese (Mn), titanium (Ti), cobalt (Co), nickel (Ni), wolfram (W) and tin (Sn); graphite or graphite intercalation compounds; and metal oxides, such as, for example, ITO and tin oxide. Particularly preferable is the use of aluminium as the cathode layer.

The application of the emitter layer, of the electron injection layer and of the cathode injection layer can be carried out in a manner known to a person skilled in the art, preferably through vapour coating such as is described, for instance, in WO-A-2009/0170244.

A contribution towards solving the above mentioned objects is also made by a conductive layer comprising at least one compound according to the present invention. According to a preferred embodiment of the conductive layer according to the present invention the conductive layer further comprises at least one conductive polymer, wherein those conductive polymers are preferred that have already been mentioned as preferred conductive polymers I) in connection with the composition according to the present invention. In this context it is also preferred that the weight ratio of the at least one compound according to the present invention and the at least one conductive polymer (in case of a polythiophene/(poly)anion complex the weight ratio of the at least one compound according to the present invention and the total weight of polythiophene and polyanion) in the conductive layer is preferably in the range from 1:100 to 100:1, more preferably in the range from 1:10 to 10:1 and most preferably in the range from 1:5 to 5:1.

A contribution towards solving the above mentioned objects is also made by a an electronic component comprising a conducting layer obtainable by the process according to the present invention or comprising a conductive layer according to the present invention. According to a preferred embodiment of the electronic component according to the present invention this electronic component is an OLED, a display, an organic solar cell, a hybrid solar cell, a field effect transistor, or a thermoelectric generator. In case of an OLED it is furthermore preferred that the hole injection layer of the OLED is obtainable by the process according to the present invention or corresponds to a conductive layer according to the present invention.

A contribution towards solving the above mentioned objects is also made by the use of at least one compound according to the present invention as an as an additive in a hole injection layer of an OLED.

The invention will now be further illustrated by means of non-limiting examples.

EXAMPLES

Example 1A Synthesis of Compound Xa

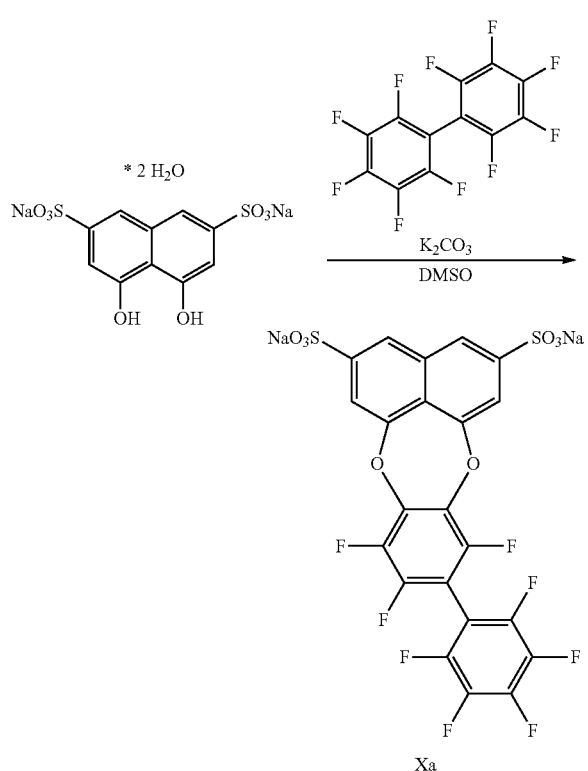

Chromotropic acid disodium salt (2.00 g, 0.005 mol), potassium carbonate (2.76 g, 0.005 mol), decafluorobiphenyl (8.35 g, 0.025 mol) and 50 ml of DMSO were stirred under heating at 120-130° C. during 40 hours. The reaction was controlled by $^1$H-NMR spectroscopy. After completion of the reaction it was cooled down to room temperature and filtered from the solid, containing the rest of $K_2CO_3$ and the by-product KF. DMSO from the filtrate was evaporated under vacuum (1 mbar) and excess of decafluorobiphenyl was sublimed. 20 mL of water were added to the residue and the product was precipitated as a white solid, which was filtered and washed with cold water. The filter cake was dried under vacuum to give 2.27 g of the pure compound Xa, which correspond to the isolated yield of 69%.

$^1$H NMR (300 MHz, DMSO-d6) δ=8.12 (s, 2H), 7.65 (d, J=15.9 Hz, 2H); $^{19}$F NMR (282 MHz, DMSO-d6) δ=−55.6 (m), −59.5 (m), −60.2 (m), −70.0 (m), −78.7 (m), −82.7 (m).

Prior to formulation compound Xa was recrystallized. It was dissolved in $H_2O$ (solid content 1%) and heated to 90° C. The hot solution was filtered through a syringe filter (PVDF, 0.8 μm) and concentrated.

Example 1B Synthesis of Compound Xe

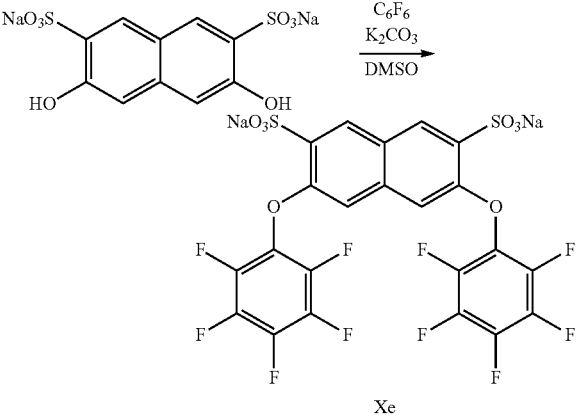

3,6-Dihydroxynaphthalene-2,7-disulfonic acid disodium salt was reacted with hexafluorobenzene and potassium carbonate (1:4:10 mole ratio) in DMF (at concentration of 40 g of 3,6-dihydroxynaphthalene-2,7-disulfonic acid disodium salt per 1 L of DMF) at 130° C. The reaction was controlled by $^1$H-NMR spectroscopy. After 20 h of heating at 120-130° C. the reaction was complete according to $^1$H-NMR spectroscopy. The mixture was cooled to room temperature and filtered from the solid, containing the rest of $K_2CO_3$ and the by-product KF. DMSO and the excess of hexafluorobenzene from the filtrate were evaporated under vacuum (1 mbar). Water (10 mL per 25 mL of the initial amount of DMSO) was added to the residue and the product was precipitated as a white solid, which was filtered, washed with water and dried under vacuum (1 mbar) to give the first portion of compound Xe. The filtrate formed was evaporated up to approximately 50% of its initial volume and cooled overnight in the refrigerator at 4° C. A new portion of the product was precipitated as a white solid, which was filtered again, washed with water and dried in vacuum (1 mbar) to give the second portion of compound Xe as a white solid. The total yield of compound Xe was 67%.

$^1$H NMR (300 MHz, DMSO) δ 8.31 (s, 2H), 7.07 (s, 2H); $^{19}$F NMR (282 MHz, DMSO) δ=−76.0 (m), −83.0 (m), −84.3 (m).

Example 1C Synthesis of Compound Xg (Soluble in Organic Solvents)

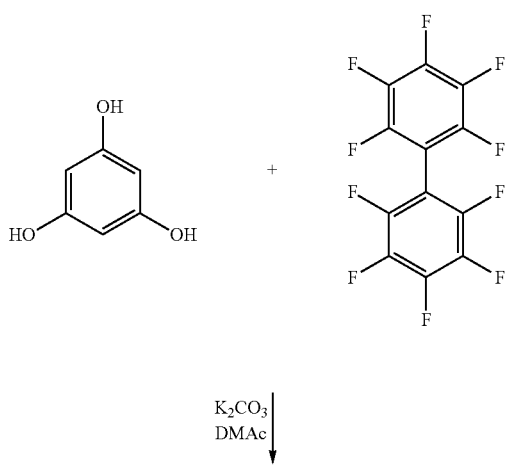

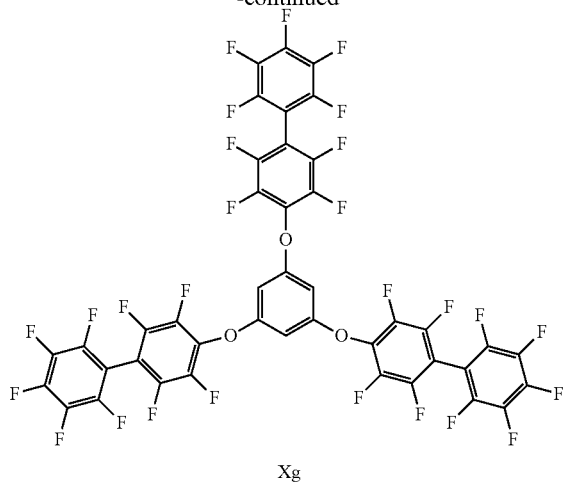

Xg

K$_2$CO$_3$ (1.1 g, 0.008 mol) and decafluorobiphenyl (3 g, 0.009 mol) were suspended in dry N,N-dimethylacetamide (10 ml) and heated to 100° C. 1,3,5-Trihydroxybenzene (0.25 g, 0.002 mol) dissolved in DMAc (10 ml) was added slowly over a period of 4 h at 92-97° C. After complete addition the reaction mixture was heated to 120° C. until TLC confirmed complete consumption of starting material. The mixture was concentrated and to the residue a dilute NH$_4$Cl-solution (1 g NH$_4$Cl/20 ml H$_2$O) was slowly added. The aqueous phase was extracted 3 times with MTBE. The combined organic layers were washed with brine and dried over Na$_2$SO$_4$. After evaporation of solvents the clear yellow highly viscous oil was purified by column chromatography over SiO$_2$ (eluent: toluene). The product was isolated as a light yellow highly viscous oil (2.1 g, 0.002 mol, quant.).

LC-MS (ESI; H$_2$O/MeCN Grad. 0.8 g/L NH4OAc) M=1068; $^1$H NMR (400 MHz, CDCl$_3$): δ=6.49.

Example 2

Formulation of a Dispersion of PEDOT:PSS with Compound Xa

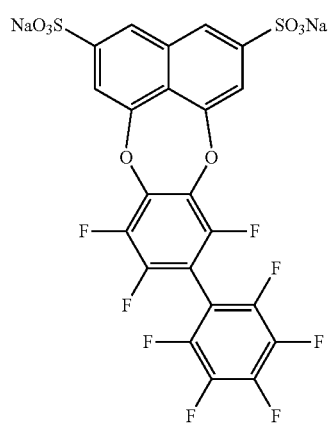

Xa

Example 2A (Solid Content of Compound Xa=0.7%)

0.42 g of compound Xa were dissolved in 30 g Clevios P VPAI 4083 (Heraeus Precious Metals GmbH & Co. KG, 1.5% solid content). 24 g of water were added and the mixture was stirred for 30 min at room temperature and then heated (1 h, 40° C.) until all solids were dissolved completely. The mixture was cooled to room temperature (1 h), 6 g of ethanol were added and the mixture was stirred for another 30 min. After aging for 3 h the dispersion was filtered subsequently through 0.8 μm and 0.45 μm syringe filters (PVDF).

Example 2B (Solid Content of Compound Xa=0.47%)

0.28 g of compound Xa were dissolved in 40 g Clevios P VPAI 4083 (Heraeus Precious Metals GmbH & Co. KG, 1.5% solid content). 14 g of water were added and the mixture was stirred for 30 min at room temperature and then heated (1 h, 40° C.) until all solids were dissolved completely. The mixture was cooled to room temperature (1 h), 6 g of ethanol were added and the mixture was stirred for another 30 min. After aging for 3 h the dispersion was filtered subsequently through 0.8 μm and 0.45 μm syringe filters (PVDF).

Example 2C (Solid Content of Compound Xa=0.3%)

0.18 g of compound Xa were dissolved in 40 g Clevios P VPAI 4083 (Heraeus Precious Metals GmbH & Co. KG, 1.5% solid content). 14 g of water were added and the mixture was stirred for 30 min at room temperature and then heated (1 h, 40° C.) until all solids were dissolved completely. The mixture was cooled to room temperature (1 h), 6 g of ethanol were added and the mixture was stirred for another 30 min. After aging for 3 h the dispersion was filtered subsequently through 0.8 μm and 0.45 μm syringe filters (PVDF).

Example 2D (Solid Content of Compound Xa=1.05%)

0.63 g of compound Xa were dissolved in 30 g Clevios P VPAI 4083 (Heraeus Precious Metals GmbH & Co. KG, 1.5% solid content). 24 g of water were added and the mixture was stirred for 30 min at room temperature and then heated (1 h, 55° C.) until all solids were dissolved completely. The mixture was cooled to room temperature (1 h), 6 g of ethanol were added and the mixture was stirred for another 30 min. After aging for 3 h the dispersion was filtered through a 0.8 μm syringe filter (PVDF). For filtration through 0.45 μm syringe filter 3 h ultrasonic treatment (Sonorex R1028, Bandelin) was necessary prior to filtration.

Example 3

Fabrication of an OLED with a Conductive Layer Containing Compound Xa

The dispersion obtained in Examples 2A-2D was used to construct organic light emitting diodes (OLEDs). The procedure for producing the OLEDs was as follows:

i) Preparation of the Substrate

ITO-coated glass is cut into pieces 50 mm×50 mm in size (substrates) and is structured with photo resist into 8 contact lines—each 2 mm in width at their ends. Thereafter, the substrates are cleaned in 0.3% strength Mucasol solution in an ultrasound bath, rinsed with distilled water and spin-dried in a centrifuge. Immediately before coating, the ITO-coated sides are activated for 10 min in a UV/ozone reactor (PR-100, UVP Inc., Cambridge, GB).

ii) Application of the Hole-Injecting Layer

About 5 ml of the dispersion according to Examples 2A-2D are filtered (Millipore HV, 0.45 μm). The cleaned ITO-coated substrate is laid on a spin-coater (Carl Süss RC8) and the filtered solution is distributed on the ITO-coated side of the substrate. The excess solution is then spun off by rotating the plate for 30 sec. The spin-speed was adjusted to obtain always a layer thickness of 50 nm (dried film) determined with a stylus profilometer (Dektak 150, Bruker). Thereafter, the substrate coated in this way is dried on a hotplate at 200° C. for 5 min.

iii) Application of the Hole Transport and the Emitter Layer

The ITO substrates coated with the dispersion from Examples 2A-2D are transferred into a vapor deposition unit (Univex 350, Leybold). Under a pressure below $10^{-3}$ Pa, first 60 nm of a hole transport layer of NPB (N,N'-bis(naphthalen-1-yl)-N,N'-bis(phenyl)-benzidine) and then 50 nm of an emitter layer of AlQ3 (tris-(8-hydroxyquinoline)-aluminium) are vapor-deposited in succession at a vapor deposition rate of 1 Å/sec.

iv) Application of the Metal Cathode

The layer system is then transferred into a glove box with an $N_2$ atmosphere and an integrated vapor deposition unit (Auto306 Vacuum Coater, Edwards), and metal electrodes are vapor-deposited. For this, the substrate is laid on a shadow mask with the layer system downwards. The shadow mask comprised rectangular slots of 2 mm width which intersected the ITO strips and are orientated perpendicular to these. A 0.5 nm thick LiF layer and then a 200 nm thick Al layer are vapor-deposited successively from two vapor deposition boats under a pressure of $p<=10^{-3}$ Pa. The vapor deposition rates were 1 Å/s for LiF and 10 Å/s for Al. The area of the individual OLEDs is 4.0 mm².

v) Layer Stack Overview

Example 3A ITO//Formulation from Example 2A (50 nm)//NPBNALQ//LiF//Al

Example 3B ITO//Formulation from Example 2B (50 nm)//NPBNALQ//LiF//Al

Example 3C ITO//Formulation from Example 2C (50 nm)//NPBNALQ//LiF//Al

Example 3D ITO//Formulation from Example 2D (50 nm)//NPBNALQ//LiF//Al vi) Characterization of the OLED The two electrodes of the organic LED are connected (contacted) to a source/measuring unit (Keithley 2400) via electrical leads. The positive pole is connected to the ITO electrode and the negative pole is connected to the metal electrode. The dependency of the OLED current and the electroluminescence intensity (detection is with a photodiode (EG&G C30809E)+electrometer (Keithley 6415)) on the voltage is plotted. The lifetime of the OLED-device is then determined by allowing a constant current of I=3.84 mA to flow through the arrangement and monitoring the voltage and light intensity as a function of time.

The characteristic Data for the OLEDs is summarized in table 1.

Comparative Example 4

Fabrication of an OLED not Containing Compound Xa

The procedure is the same as in Example 3, with the difference that in the second process step Clevios P VP AI4083 (Heraeus Precious Metals GmbH & Co. KG), regarded as standard in OLED construction, was used solely as the interlayer instead of the dispersions according to the invention from example 2A-2D. Clevios© P VP AI4083 was deposited according to Example 3. The film thickness was 50 nm.

The characteristic Data for the OLEDs is summarized in table 1.

Layer Stack:

Comparative Example 4

ITO//Clevios P VP AI4083 (50 nm)//NPB//ALQ//LiF//Al

Example 5

Determination of Resistivity

The resistivity of Clevios™ films is determined by measuring the film's sheet resistance and its layer thickness. The films are prepared by depositing 1-2 ml of the polymer dispersion on a 50 mm×50 mm glass-substrate. Prior deposition the glass-substrate of 1 mm thickness is thoroughly cleaned in 0.3% strength Mucasol solution in an ultrasound bath, rinsed with distilled water and spin-dried in a centrifuge. As a final step the surface to be coated on is activated by UV/Ozone exposure (PR-100UV/Ozone UVP, Cambridge, GB) for 15 min. Next the glass-substrate is placed in a chuck of a spin-coater (Carl Süss RC8). The overlaying dispersion is removed by rotating the glass-plate at 1000 rpm for 30 sec. A thin uniform film is obtained. The film is conveyed to a heat-plate set to 130° C. and left there for 5 min to dry.

In a next step the film is covered with a shadow mask. The mask is made of a 100 μm-thick steel-sheet of size 50 mm×50 mm exhibiting 6 parallel slits machined in the centre (Length L: 25.0 mm, width b: 3.0 mm, slit-separation: a=500 μm). The mask is held by a magnet from the backside of the coated substrate. The substrate is mounted in a vacuum-evaporator with electro-thermally heated boats for Ag-evaporation (Univex 350, Leybold). The vessel is evacuated to a pressure of $6 \times 10^{-4 \circ}$ Pa. When this pressure is reached, Ag is thermally evaporated at a rate of 20 Å/sec until a final electrode-thickness of 2000 Å is reached.

The resistance R between adjacent Ag-electrodes is measured with an electrometer (Keithley 616) in a home-built set-up in which the sample is mounted in a vacuum chamber and Au-contact pins are pressed on the Ag-electrodes.

The film's thickness d is determined by scratching the film off the substrate with a razor blade and scanning the stylus of a mechanical profilometer (Dektak 150, Bruker) across the scratch.

Finally the resistivity "ro" is calculated my multiplying the sheet resistance with the layer thickness according to ro=R×L/b×d.

The resistivities of films made of dispersions according to Example 2A-2D are shown in table 1.

Example 6

Comparison of the OLEDs from Examples 3 and 4

The graphs plotting current and electroluminescence against voltage and the lifetime measurements for the OLEDs from Examples 3 and 4 were compared.

TABLE 1

| | specific resistance (Ohm × cm) | IVL-Characteristics at U = 5.0 V | | | Lifetime @ I = 48 mA/cm² | | | |
|---|---|---|---|---|---|---|---|---|
| | | I (mA/cm²) | L (cd/m²) | Efficiency (cd/A) | U (t = 0) (Volt) | L (t = 0) (cd/m²) | t (80%) (h) | t (50%) (h) |
| Ex. 3A | 0.13 | 1.48 | 1.58 | 1.05 | 0.90 | 1.01 | 2.2 | 2.6 |
| Ex. 3B | 0.11 | 1.33 | 1.24 | 0.93 | 0.95 | 0.93 | 2.79 | 2.94 |
| Ex. 3C | 0.1 | 1.3 | 1.34 | 1.03 | 0.90 | 0.92 | 2.2 | 2.18 |
| Ex. 3D | 0.1 | 1.5 | 1.72 | 1.14 | 0.89 | 1.01 | 1.8 | 2.57 |
| Comp. Ex. 4 (AI4083) | 1 | 1 | 1 | 1 | 1 | 1 | 1 | 1 |

OLED-characteristics from Examples 3 and 4 wherein the values were normalized to the comparative example 4.

A significant increase of lifetime compared to the standard (Comparative Example 4) can be observed for all Examples 3A-3D.

The invention claimed is:

1. A composition comprising

I) at least one conductive polymer, wherein the conductive polymer comprises a complex of poly(3,4-ethylenedioxythiophene) (PEDOT) and polystyrenesulfonic acid (PSS), II) water, and III) at least one compound selected from the group consisting of formulae Xa to Xf, or a salt thereof

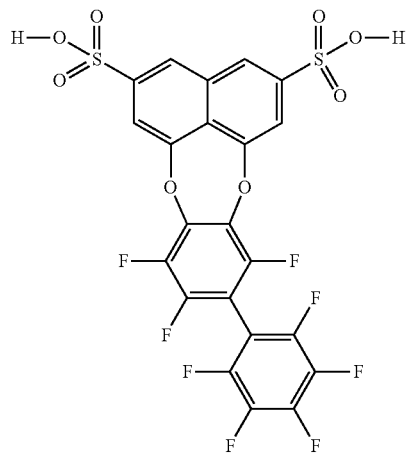

Xa

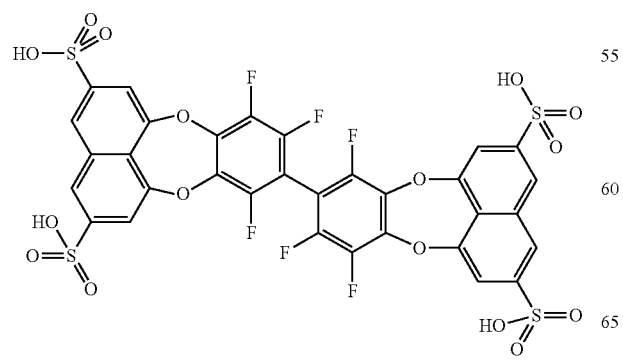

Xb

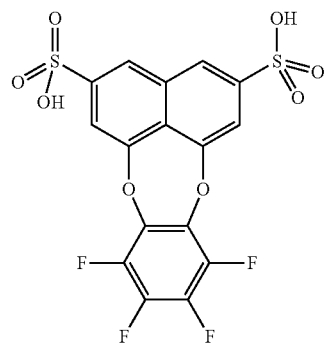

Xc

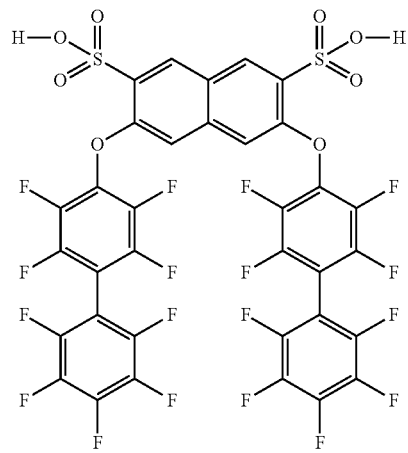

Xd

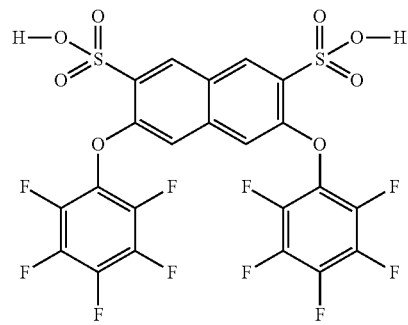

Xe

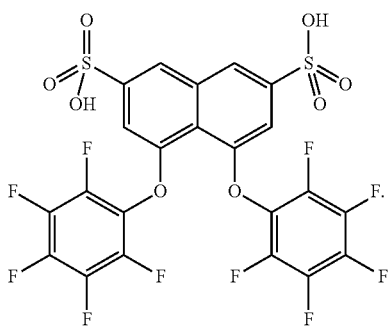

Xf

2. A process for the preparation of a conductive layer, comprising the process steps:

(P1) superimposing a substrate with the composition according to claim 1; and (P2) at least partially removing the solvent.

3. A conductive layer comprising a composition according to claim 1.

4. An electronic component comprising a conducting layer obtained by the process according to claim 2.

5. The electronic component according to claim 4, wherein the electronic component is an OLED, a display, an organic solar cell, a hybrid solar cell, a field effect transistor, or a thermoelectric generator.

6. An organic solar cell comprising a hole-injection layer, wherein an additive in the hole-injection layer comprises a composition according to claim 1.

7. An OLED comprising a hole-injection layer, wherein an additive in the hole-injection layer comprises a composition according to claim 1.

8. An electronic component comprising a conductive layer according to claim 3.

9. A process for the preparation of a conductive layer, comprising the process steps:

(P1) superimposing a substrate with a composition comprising water and a compound selected from the group consisting of formulae Xa to Xf, or a salt thereof (P2) at least partially removing the water;

(P3) superimposing the substrate with a composition according to claim 1, or with a composition comprising a water and a conductive polymer, wherein the conductive polymer comprises a complex of poly(3,4-ethylenedioxythiophene) (PEDOT) and polystyrenesulfonic acid (PSS); and (P4) at least partially removing the water.

10. A process for the preparation of a conductive layer, comprising the process steps:

(P1) superimposing a substrate with a composition comprising a water and a conductive polymer, wherein the conductive polymer comprises a complex of poly(3,4-ethylenedioxythiophene) (PEDOT) and polystyrenesulfonic acid (PSS), (P2) at least partially removing the water;

(P3) superimposing the substrate with the composition according to claim 1, or with a composition comprising water and a compound selected from the group consisting of formulae Xa to Xf, or a salt thereof

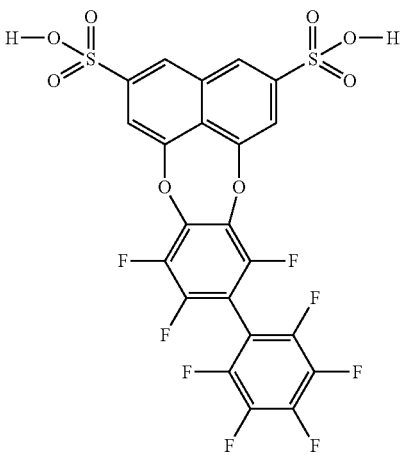

Xa

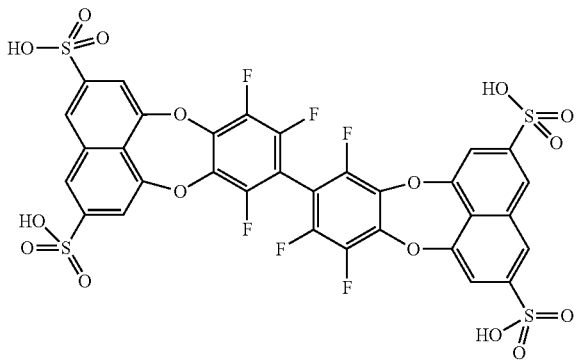

Xb

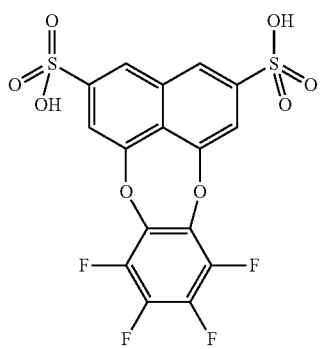

Xc

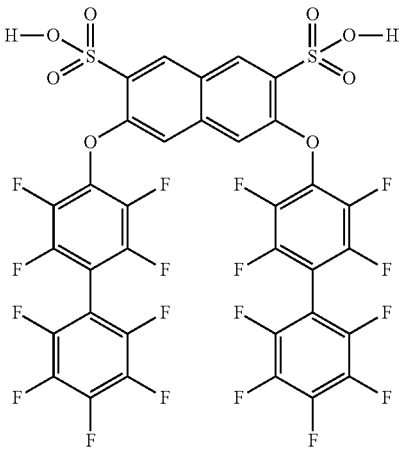

Xd

-continued
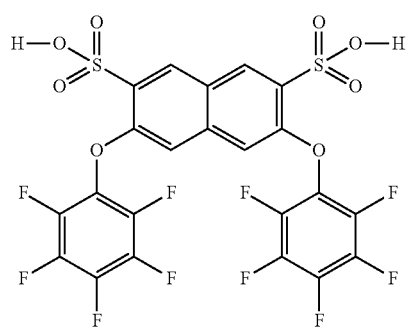
Xe
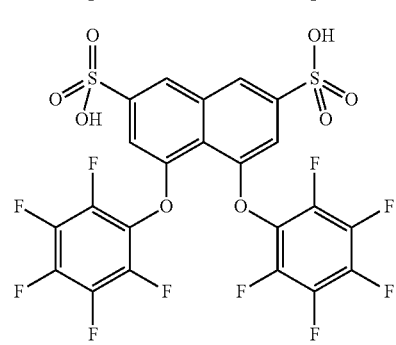
Xf
and
(P4) at least partially removing the water.
* * * * *